United States Patent
Jurecic et al.

(10) Patent No.: US 6,872,812 B2
(45) Date of Patent: Mar. 29, 2005

(54) HEPP, A NOVEL GENE WITH A ROLE IN HEMATOPOIETIC AND NEURAL DEVELOPMENT

(75) Inventors: Roland Jurecic, Key Biscayne, FL (US); Ronald G. Nachtman, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 10/076,069

(22) Filed: Feb. 15, 2002

(65) Prior Publication Data

US 2002/0177214 A1 Nov. 28, 2002

Related U.S. Application Data

(60) Provisional application No. 60/268,923, filed on Feb. 16, 2001.

(51) Int. Cl.[7] ..................... A07H 21/02; C07H 21/04; A01K 67/027
(52) U.S. Cl. ........................... 536/23.1; 800/18
(58) Field of Search ............................ 536/23.1; 800/18

(56) References Cited

PUBLICATIONS

Isomura, Genbank Accession AP000070, first published Apr. 8, 1999.*
Ngo, in The Protein Folding Problem and Tertiary Structure Prediction, Merz et al. (eds.), Birkhauser Boston: Boston, MA, pp. 433 and 492–495, 1994.*
Rudinger in Peptide Hormones, Persons (ed.), University Park Press: Baltimore, MD, pp. 1–7, 1976.*
Akaboshi, 2003, Human Mutation, vol. 22, pp. 442–450.*
Sequence alignment SEQ ID NO:1 with Kargul, Jan. 2001, Genbank Accession No. BG069072.*
Sequence alignment SEQ ID NO:1 with Kargul, Jan. 2001, Genbank Accession No. BG082096.*
Arakawa, Jun. 2000, Genbank Accession No. BB055758.*
Yahyawi, Dec. 2000, Genbank Accession No. BF607870.*
Sequence alignment SEQ IQ NO:1 with Gallatin, 1998, USPN 5,831,029, SEQ ID NO: 45.*
James M. Abdullah, et al., "Cloning and Characterization of hepp, a Novel Gene Expressed Preferentially in Hematopoietic Progenitors and Mature Blood Cells", Blood Cells, Molecules and Diseases, 27(3), May/Jun. 2001, pp. 667–676.
GenBank Data Entry, Access No. AF322238 (Jul. 5, 2001).
GenBank Data Entry, Access No. AF 322239 (Jul. 5, 2001).
GenBank Data Entry, Access No. AK000771 (Feb. 22, 2000).

* cited by examiner

*Primary Examiner*—Joseph Woitad
*Assistant Examiner*—Valarie Bertoglio
(74) *Attorney, Agent, or Firm*—Venable LLP; Ann S. Hobbs

(57) ABSTRACT

The invention is directed to an isolated gene and protein product, designated Hepp, which has a role in mammalian hematopoiesis and neural function, and is further directed to a genetically modified non-human mammal that is homozygous or heterozygous for a disruption in the endogenous Hepp gene.

6 Claims, 16 Drawing Sheets

FIG. 1A

```
   1 CCCCGCGTCGGTCTTCCACCTCACCTTTCGAGCTGGCCGCCGCTTGCTGTGCGCAGTTTC     60
  61 GGGGGACTGGACCTTCCCTGGCTTTTAGCAGCGCCGAGCGCCATGGCGACCCTTTGCTGG    120
 121 GCAGGTGACCGATTCCGGGTGCCCGAAGGAGCTGGCGTGGGTCTGCCTTGCAGCCGCCCG    180
 181 CCTGGACAGGATGTTTGCTAGAGGGCTGAAGAGGAAATATGGTGACCAGGAAGAAGGAGT    240
   1             M  F  A  R  G  L  K  R  K  Y  G  D  Q  E  E  G  V    17
 241 AGAGGGTTTTGGCACTGTCCCTTCCTATAGCCTGCAGCGACAGTCACTCCTGGACATGTC    300
             E  G  F  G  T  V  P  S  Y  S  L  Q  R  Q  S  L  L  D  M  S    37
 301 CCTTGTCAAGCTCCAGCTCTGTCACATGCTAGTGGAGCCCAATCTCTGCCGCTCGGTCCT    360
             L  V  K  L  Q  L  C  H  M  L  V  E  P  N  L  C  R  S  V  L    57
 361 CATCGCCAACACAGTCCGGCAGATCCAGGAGGAAATGAGCCAGGATGGTGTGTGGCATGG    420
             I  A  N  T  V  R  Q  I  Q  E  E  M  S  Q  D  G  V  W  H  G    77
 421 GATGGCACCCCAGAATGTAGATCGGGCACCAGTTGAACGCCTGGTGTCCACAGAGATCCT    480
             M  A  P  Q  N  V  D  R  A  P  V  E  R  L  V  S  T  E  I  L    97
 481 GTGTCGTACAGTGAGGGGAGCTGAGGAAGAGCACCCTGCTCCTGAACTGGAAGATGCTCC    540
             C  R  T  V  R  G  A  E  E  E  H  P  A  P  E  L  E  D  A  P   117
 541 CTTGCAAAACTCGGTTTCCGAGCTCCCCATCGTTGGCTCAGCACCAGGGCAAAGGAACCC    600
             L  Q  N  S  V  S  E  L  P  I  V  G  S  A  P  G  Q  R  N  P   137
 601 TCAGAGCAGCCTCTGGGAGATGGACAGCCCACAAGAAAACAGGGGAAGCTTTCAGAAGTC    660
             Q  S  S  L  W  E  M  D  S  P  Q  E  N  R  G  S  F  Q  K  S   157
 661 ACTGGACCAGATATTTGAGACCCTGGAGAACAAAAACTCCAGTTCAGTGGAGGAACTCTT    720
             L  D  Q  I  F  E  T  L  E  N  K  N  S  S  S  V  E  E  L  F   177
 721 CTCAGATGTGGACAGCTCCTACTATGACCTGGACACAGTGCTAACAGGAATGATGAGTGG    780
             S  D  V  D  S  S  Y  Y  D  L  D  T  V  L  T  G  M  M  S  G   197
 781 GACCAAGTCCAGTCTCTGCAATGGCCTTGAGGGCTTTGCTGCAGCCACCCCTCCTCCCAG    840
             T  K  S  S  L  C  N  G  L  E  G  F  A  A  A  T  P  P  P  S   217
 841 TTCCACTTGCAAGTCTGACCTGGCTGAGCTGGACCATGTGGTAGAGATTCTGGTGGAGAC    900
             S  T  C  K  S  D  L  A  E  L  D  H  V  V  E  I  L  V  E  T   237
 901 CTGAGAGGCCACCCCAGTGGGCTAAGGGTGAGGCCACCAGTCCCCATGGAGCTCACGTGT    960
         *
 961 GTTGTGACCCAGAGACAGATAAGCACTTGTCCTAAGAGGGGCTCTGGCTCTTGAGCTCAT   1020
1021 TATCCTTTTGTGTGACATTGGACTCACTGTGGAGGATGGTGTGTCACAGCTATGTCTAGT   1080
1081 CTATTTTCAATTAGATAGGTGAACTTTCTAAAATTAAGTTTTATATGTTTTTGGGCAATA   1140
1141 TTTTGTCTTAAGATATATTTTTTAAACTTTTTATACTTTAGATTTTTTTCAGCTATTTTC   1200
1201 TTAAAAGTATATTTTTTTCTACAAACATCCTCTGCTGCTACATTAGAAACATTTATAACCT   1260
1261 AAATACGATTGGTGTGTCATTTTAAAGGTTTAAATAGAAAACTTCTTTTGTTACTGAGTC   1320
1321 TCTACACTCCCAAGGCAACTGTAAATGTAGCCGGCCGGTGTTTACATGAGAGGCTCCAG   1380
1381 TATGGTCTACATTCTAGTAGAGCTTGAAAAGAAACCATGCACAGCTCCACTGCCCCCTCAC   1440
1441 TGGGTCTGCTCTGGCGGATCGGAGCTCTCTTCCTAGCCCCGTGTGCAGGATGGCTTTATT   1500
1501 TATGCCTATTTATATGTAAATGCCACTGAAAGCTAAGGTCTTACTCCTGGAAATCCCAAC   1560
1561 ACCAGTTCTTCAGGGACTGCTGTGAGGCAGTGCCTTATGCAGGTCTTGTCCTTGGCCATC   1620
1621 ACTGTCTGGTTCCCAGCCCAGCACATGTGACATGAGGACATGACATGCCCGAACCACCCA   1680
1681 GCACCACATGCTCCATGTCAAGTGTGTACGTGGAGACCACTGGCTCCCAGGCCTGTGCTC   1740
1741 AGAGAGGGTGTGCAGTCCTACGTGTGCTGGGGGGACGACGGTGACCTGTGCTTGCTTGC   1800
1801 TTTTAAAATGGTGCTTGGACGTTTTAAGGTTAAAAACAATCCGACTCCATATGATTTAGG   1860
1861 GCTCCTCCACCCTGGGGTGGCCCCTATGCTGTCTGCTTGGATCTCAAAGTCTTGGTACTC   1920
1921 GGCACTGTCAGACTCCACCCCATGTATCCTTTTTGTTTCTCTTGTGCTTTTTTTGGACTT   1980
1981 CCCAACCTGAGCCTAAGGTTTTATTTTATATGTGCTTCAATATCAACAATGTAAACCTCA   2040
2041 CTTTATTAAAAGTATCCAGCAAATGGAAAAAAAAAAAAAAAA
```

FIG. 1B

```
   1 GGGAAGCTGGCGGCACAGCCGTGGCGCCTGGCTGAGCAGAGGACCCGGCGGGCGGCCTCG    60
  61 CGGGTCAGGACACAATGTTTGCACGAGGACTGAAGAGGAAATGTGTTGGCCACGAGGAAG   120
   1                 M  F  A  R  G  L  K  R  K  C  V  G  H  E  E  D    16
 121 ACGTGGAGGGAGCCCTGGCCGGCTTGAAGACAGTGTCCTCATACAGCCTGCAGCGGCAGT   180
        V  E  G  A  L  A  G  L  K  T  V  S  S  Y  S  L  Q  R  Q  S    36
 181 CGCTCCTGGACATGTCTCTGGTGAAGTTGCAGCTTTGCCACATGCTTGTGGAGCCCAACC   240
        L  L  D  M  S  L  V  K  L  Q  L  C  H  M  L  V  E  P  N  L    56
 241 TGTGCCGCTCAGTCCTCATTGCCAACACGGTCCGGCAGATCCAAGAGGAGATGACGCAGG   300
        C  R  S  V  L  I  A  N  T  V  R  Q  I  Q  E  E  M  T  Q  D    76
 301 ATGGGACGTGGCGCACAGTGGCACCCCAGGCTGCAGAGCGGGCGCCGCTCGACCGCTTGG   360
        G  T  W  R  T  V  A  P  Q  A  A  E  R  A  P  L  D  R  L  V    96
 361 TCTCCACGGAGATCCTGTGCCGTGCAGCGTGGGGGCAAGAGGGGGCACATCCTGCTCCTG   420
        S  T  E  I  L  C  R  A  A  W  G  Q  E  G  A  H  P  A  P  G   116
 421 GCTTGGGGGACGGCCACACACAGGGTCCAGTTTCTGACCTTTGCCCAGTCACCTCAGCAC   480
        L  G  D  G  H  T  Q  G  P  V  S  D  L  C  P  V  T  S  A  Q   136
 481 AGGCACCAAGGCACCTGCAGAGCAGCGCCTGGAGATGGATGGCCCTCGAGAAAACAGAG   540
        A  P  R  H  L  Q  S  S  A  W  E  M  D  G  P  R  E  N  R  G   156
 541 GAAGCTTTCACAAGTCACTTGATCAGATATTTGAAACGCTGGAGACTAAAAACCCCAGCT   600
        S  F  H  K  S  L  D  Q  I  F  E  T  L  E  T  K  N  P  S  C   176
 601 GCATGGAAGAGCTGTTCTCAGACGTGGACAGCCCTACTACGACCTGGACACAGTACTGA   660
        M  E  E  L  F  S  D  V  D  S  P  Y  Y  D  L  D  T  V  L  T   196
 661 CAGGCATGATGGGGGGTGCCAGGCCGGCCCCTGCGAAGGGCTCGAGGGCTTGGCTCCGG   720
        G  M  M  G  G  A  R  P  G  P  C  E  G  L  E  G  L  A  P  A   216
 721 CCACCCCAGGCCCTAGCTCCAGCTGCAAGTCCGACCTGGGCGAGCTGGACCACGTGGTGG   780
        T  P  G  P  S  S  S  C  K  S  D  L  G  E  L  D  H  V  V  E   236
 781 AGATCCTGGTGGAGACCTGAGCAGGAGCCCTGAGTGCTCACAGCCGCCTCTGACGCATTG   840
        I  L  V  E  T  *                                               241
 841 ACACGTGAGCACTGGCTCCCACGGAGGGGTGCGCCCTGCCGCCAGCGGCCCAGCCTTGCTGC   900
 901 CCTGTCTGCTGATTCTGAGAAAATCCCAGAACAGCCCATTACCAGTGGGCTGCAGCCCTA   960
 961 GGCCCGTCCCACTCACCCTCCCCCCTGTGGAGCGCCAGGCAGAGGCTGTTCTGGAAGGCTT  1020
1021 CTTGTCTTCTGACGTCCCCACAGCCCTGGGCCCCTCGTGTCTCTTTGTGTCCCCACTGT  1080
1081 AGAGGACGGTGAGCCGCAGCTGCATCAACCTCCTTTTACCTTTAGATAGGTGAATTTTTA  1140
1141 CAATTCAGTTTTACATGTTTTGGGCAGTATTTTGTCTTAAGATATATTTTTTAAACTTTT  1200
1201 TATACCTTATCTCTTTAGATTTTTTCAGCTATTTCTTAAAAGTATATTTTTTCTATAAA  1260
1261 CATCCTTTGCTGCTACATTAGAAACTTTTTATAGCCTAAACAATTGCAGTTGGTGTGTTTCA  1320
1321 TTTTTTTTAAGGTTTAAATAAGGGTTTTTTGTTTTGTTTTGTTTTTGCAGTGAGCATCAC  1380
1381 TACAGTCTCAGTCAACAGTGTGAATGTATCATGTTTTACTTTAAATGTGTGTGTGATACT  1440
1441 TCTTCATTATGTCCTGCGCTGCAGTGAGACCTGGGTGAAAATCAGGAGCCGCACACAGCC  1500
1501 ACATCTTCCTAGACCTAAGAGTAAATTATGGAGGATTTTATTTATGTCTATTTATATGTA  1560
1561 AATGTCATTGAAGACAAAGGTCAAATATTTGTCTGTTTGTAGATCACAGGCACCAGTTGG  1620
1621 TCTTCAGGGACCTCATAGCCCCTCGGTGGTGCCTTCTCAAGGCAGTGTTCCTGGAGGCTC  1680
1681 CCATCAGGGTCAGCCCATGCACCTGCCCTGGGTGAGGAAGTAGCATTGCTGCTGGATGAG  1740
1741 AAACGCCTGCGCTGCTCTGTTAGACTGGTGCTGAAACAAAAGGTTAAGGCTAGGTTGAAG  1800
1801 TCTAGAATGAAAGAAATCTGAATCCATGTCATTCATAACCCCTTGATCTGTAGTGTCATG  1860
1861 GGTGCTGCCGCAGGCAGGGAGTGAGCTGGGGTGCCTGCAGCCTTCCACTCCTGCCCCGC  1920
1921 CTCACCCCACATGCTCCCTGTTTCTCATGCTTTCTCTAACTTCCTCACCCCTTAACCAAA  1980
1981 AAGGTGTGTTTTCTTTTGTGCATATAGCCATTCTTAAATATCAGTGATGTAAACCTCACT  2040
2041 TTATTAAAAAATTATCCAGCAAAAAAAAAAAAAAAAAAAAAA
```

FIG. 2

```
Mouse Hepp    1  MFARGLKRKYG----DQEEGVEGFGTVPSYSLQRQSLLDMSLVKLQLCHMLVEPNLCRSV
Human HEPP    1  MFARGLKRKCVGHEEDVEGALAGLKTVSSYSLQRQSLLDMSLVKLQLCHMLVEPNLCRSV Mouse Hepp   57  LIANTVRQIQEEMSQDGVMHGMAPQNVDRAPVERLVSTEILCRTVRGAEEEHPAPELEDA
Human HEPP   61  LIANTVRQIQEEMIQDGIMRITVAPQAAAERAPLDRLVSTEILCRAAWGQEGAHPAPGLGDG Mouse Hepp  117  PLQNSVSELPIVGSAPGQRNPQSSLWEMDSPQENRGSFQKSLDQIFETLENKNSSVEEL
Human HEPP  121  HTQGPVSDLCPVTSAQAPRHLQSSAWEMDGPRENRGSFHKSLDQIFETLETKNPSCMEEL Mouse Hepp  177  FSDVDSSYYDLDTVLTGMMSGIIKSSLCNGLEGFAAAATPPPSSTCKSDLAELDHVVEILVE
Human HEPP  181  FSDVDSPYYDLDTVLTGMMSGIIKSSLCNGLEGLAPATPGPSSSCKSDLGELDHVVEILVE Mouse Hepp  237  T
Human HEPP  241  T
```

FIG. 3

| | | |
|---|---|---|
| Zebrafish Hepp | 1 | MFSKGFKRKFADGGEEISDDGLVAARVASSYSLQRQSLLDMSLIKLQLCHMLVEPNLCRS |
| Mouse Hepp | 1 | MFARGLKRKYG----DQEGVEGFGTVPSYSLQRQSLLDMSLVKLQLCHMLVEPNLCRS |
| Human HEPP | 1 | MFARGLKRKCVGH-EEDVEGALAGLKTVSSYSLQRQSLLDMSLVKLQLCHMLVEPNLCRS |

| | | |
|---|---|---|
| Zebrafish Hepp | 61 | VLIANTVRQIQEEMTHDGSWEMVTEAPCGASQSPSERLVATEVLCR---------- |
| Mouse Hepp | 56 | VLIANTVRQIQEEMSQDGVWHGMAPQNVDR--APVERLVSTEILCRTVRGAEEEHPAPEL |
| Human HEPP | 60 | VLIANTVRQIQEEMTQDGTWRTVAPQAAER--APLDRLVSTEILCRAAWGQEGAHPAPGL |

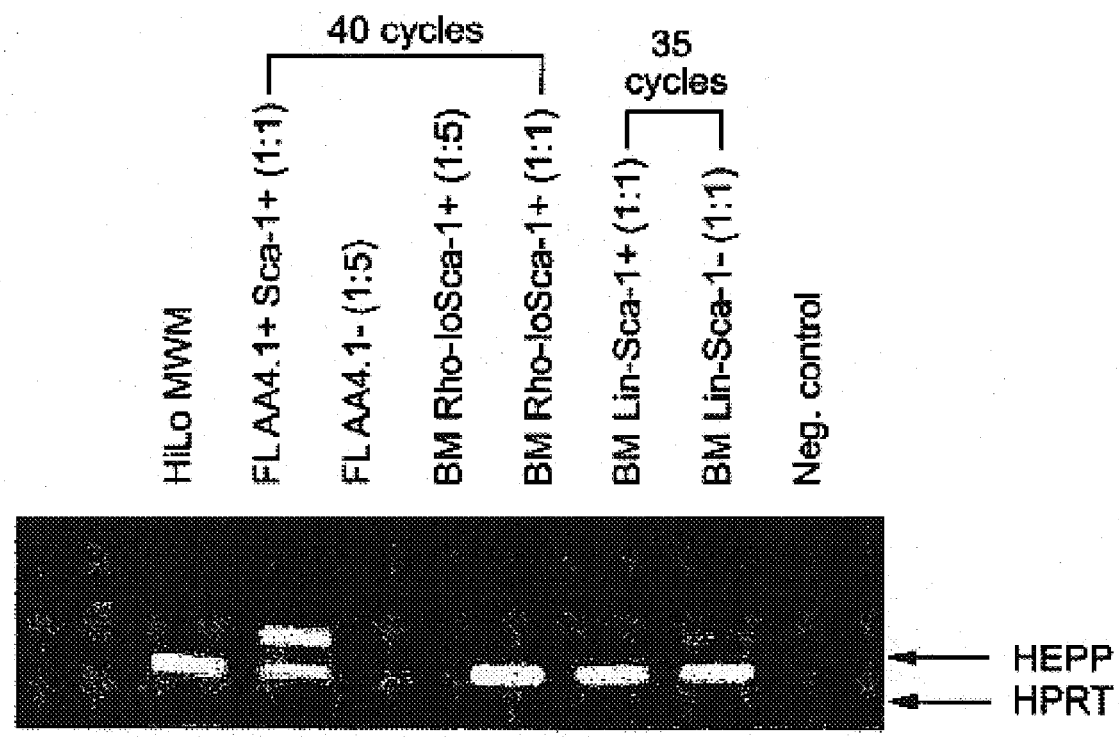

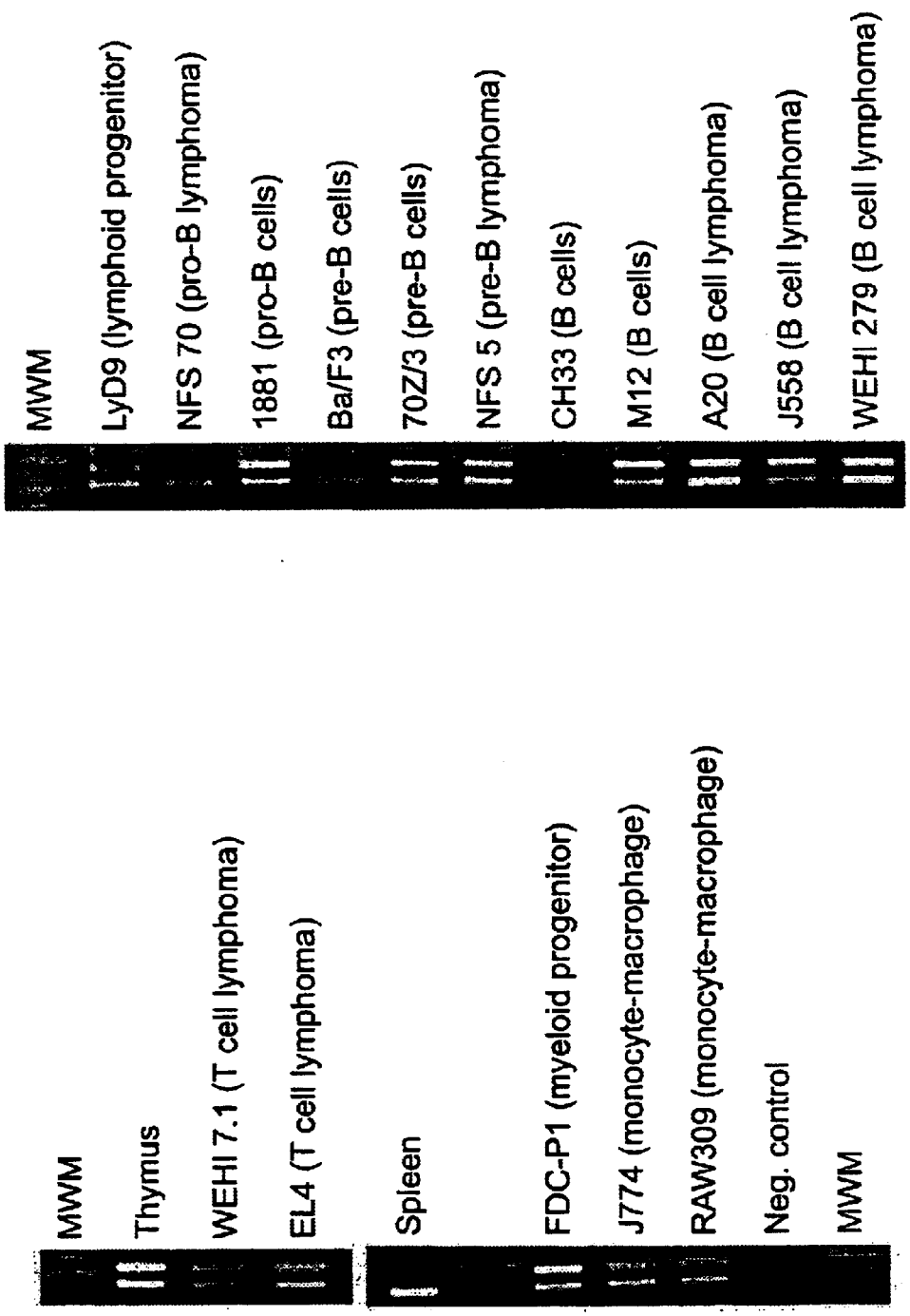

translocation breakpoints

SEQUENCE LISTING

```
<160> NUMBER OF SEQ ID NOS: 11

<210> SEQ ID NO 1
<211> LENGTH: 2082
<212> TYPE: DNA
<213> ORGANISM: Mus musculus
<220> FEATURE:
<221> NAME/KEY: CDS
<222> LOCATION: (191)..(901)

<400> SEQUENCE: 1
ccccgcgtcg gtcttccacc tcacctttcg agctggccgc cgcttgctgt gcgcagtttc      60
gggggactgg accttccctg gcttttagca gcgccgagcg ccatggcgac cctttgctgg    120
gcaggtgacc gattccgggt gcccgaagga gctggcgtgg gtctgccttg cagccgcccg    180
cctggacagg atg ttt gct aga ggg ctg aag agg aaa tat ggt gac cag       229
            Met Phe Ala Arg Gly Leu Lys Arg Lys Tyr Gly Asp Gln
              1               5                  10 gaa gaa gga gta gag ggt ttt ggc act gtc cct tcc tat agc ctg cag       277
Glu Glu Gly Val Glu Gly Phe Gly Thr Val Pro Ser Tyr Ser Leu Gln
        15                  20                  25 cga cag tca ctc ctg gac atg tcc ctt gtc aag ctc cag ctc tgt cac       325
Arg Gln Ser Leu Leu Asp Met Ser Leu Val Lys Leu Gln Leu Cys His
 30                  35                  40                  45 atg cta gtg gag ccc aat ctc tgc cgc tcg gtc ctc atc gcc aac aca       373
Met Leu Val Glu Pro Asn Leu Cys Arg Ser Val Leu Ile Ala Asn Thr
                 50                  55                  60 gtc cgg cag atc cag gag gaa atg agc cag gat ggt gtg tgg cat ggg       421
Val Arg Gln Ile Gln Glu Glu Met Ser Gln Asp Gly Val Trp His Gly
             65                  70                  75
```

```
atg gca ccc cag aat gta gat cgg gca cca gtt gaa cgc ctg gtg tcc    469
Met Ala Pro Gln Asn Val Asp Arg Ala Pro Val Glu Arg Leu Val Ser
        80                  85                  90 aca gag atc ctg tgt cgt aca gtg agg gga gct gag gaa gag cac cct    517
Thr Glu Ile Leu Cys Arg Thr Val Arg Gly Ala Glu Glu Glu His Pro
    95                 100                 105 gct cct gaa ctg gaa gat gct ccc ttg caa aac tcg gtt tcc gag ctc    565
Ala Pro Glu Leu Glu Asp Ala Pro Leu Gln Asn Ser Val Ser Glu Leu
110                 115                 120                 125 ccc atc gtt ggc tca gca cca ggg caa agg aac cct cag agc agc ctc    613
Pro Ile Val Gly Ser Ala Pro Gly Gln Arg Asn Pro Gln Ser Ser Leu
                130                 135                 140 tgg gag atg gac agc cca caa gaa aac agg gga agc ttt cag aag tca    661
Trp Glu Met Asp Ser Pro Gln Glu Asn Arg Gly Ser Phe Gln Lys Ser
            145                 150                 155 ctg gac cag ata ttt gag acc ctg gag aac aaa aac tcc agt tca gtg    709
Leu Asp Gln Ile Phe Glu Thr Leu Glu Asn Lys Asn Ser Ser Ser Val
        160                 165                 170 gag gaa ctc ttc tca gat gtg gac agc tcc tac tat gac ctg gac aca    757
Glu Glu Leu Phe Ser Asp Val Asp Ser Ser Tyr Tyr Asp Leu Asp Thr
    175                 180                 185 gtg cta aca gga atg atg agt ggg acc aag tcc agt ctc tgc aat ggc    805
Val Leu Thr Gly Met Met Ser Gly Thr Lys Ser Ser Leu Cys Asn Gly
190                 195                 200                 205 ctt gag ggc ttt gct gca gcc acc cct cct ccc agt tcc act tgc aag    853
Leu Glu Gly Phe Ala Ala Ala Thr Pro Pro Pro Ser Ser Thr Cys Lys
                210                 215                 220 tct gac ctg gct gag ctg gac cat gtg gta gag att ctg gtg gag acc    901
Ser Asp Leu Ala Glu Leu Asp His Val Val Glu Ile Leu Val Glu Thr
            225                 230                 235 tgagaggcca ccccagtggg ctaagggtga ggccaccagt ccccatggag ctcacgtgtg    961
ttgtgaccca gagacagata agcacttgtc ctaagagggg ctctggctct tgagctcatt   1021
atccttttgt gtgacattgg actcactgtg gaggatggtg tgtcacagct atgtctagtc   1081
tattttcaat tagataggtg aactttctaa aattaagttt tatatgtttt tgggcaatat   1141
tttgtcttaa gatatatttt ttaaactttt tatactttag attttttttca gctattttct   1201
taaaagtata tttttctac aaacatcctc tgctgctaca ttagaaacat ttataaccta   1261
aatacgattg gtgtgtcatt ttaaaggttt aaatagaaaa cttcttttgt tactgagtct   1321
ctacactccc aaggcaactg taaatgtagc cggccgggtt tttacatgag aggctccagt   1381
atggtctaca ttctagtaga gcttgaaaag aaccatgcac agctccactg cccctcact   1441
gggtctgctc tggcggatcg gagctctctt cctagccccg tgtgcaggat ggctttattt   1501
atgcctattt atatgtaaat gccactgaaa gctaaggtct tactcctgga aatcccaaca   1561
ccagttcttc agggactgct gtgaggcagt gccttatgca ggtcttgtcc ttggccatca   1621
ctgtctggtt cccagcccag cacatgtgac atgaggacat gacatgcccg aaccacccag   1681
caccacatgc tccatgtcaa gtgtgtacgt ggagaccact ggctcccagg cctgtgctca   1741
gagagggtgt gcagtcctac gtgtgctggg ggggacgacg gtgacctgtg cttgcttgct   1801
tttaaaatgg tgcttggacg ttttaaggtt aaaaacaatc cgactccata tgatttaggg   1861
ctcctccacc ctggggtggc ccctatgctg tctgcttgga tctcaaagtc ttggtactcg   1921
gcactgtcag actccacccc atgtatcctt tttgtttctc ttgtgctttt tttggacttc   1981
ccaacctgag cctaaggttt tatttatat gtgcttcaat atcaacaatg taaacctcac   2041
```

```
tttattaaaa gtatccagca aatggaaaaa aaaaaaaaaa a                    2082
```

<210> SEQ ID NO 2
<211> LENGTH: 237
<212> TYPE: PRT
<213> ORGANISM: Mus musculus

<400> SEQUENCE: 2

```
Met Phe Ala Arg Gly Leu Lys Arg Lys Tyr Gly Asp Gln Glu Glu Gly
 1               5                  10                  15

Val Glu Gly Phe Gly Thr Val Pro Ser Tyr Ser Leu Gln Arg Gln Ser
            20                  25                  30

Leu Leu Asp Met Ser Leu Val Lys Leu Gln Leu Cys His Met Leu Val
        35                  40                  45

Glu Pro Asn Leu Cys Arg Ser Val Leu Ile Ala Asn Thr Val Arg Gln
    50                  55                  60

Ile Gln Glu Glu Met Ser Gln Asp Gly Val Trp His Gly Met Ala Pro
65                  70                  75                  80

Gln Asn Val Asp Arg Ala Pro Val Glu Arg Leu Val Ser Thr Glu Ile
                85                  90                  95

Leu Cys Arg Thr Val Arg Gly Ala Glu Glu His Pro Ala Pro Glu
            100                 105                 110

Leu Glu Asp Ala Pro Leu Gln Asn Ser Val Ser Glu Leu Pro Ile Val
        115                 120                 125

Gly Ser Ala Pro Gly Gln Arg Asn Pro Gln Ser Ser Leu Trp Glu Met
    130                 135                 140

Asp Ser Pro Gln Glu Asn Arg Gly Ser Phe Gln Lys Ser Leu Asp Gln
145                 150                 155                 160

Ile Phe Glu Thr Leu Glu Asn Lys Asn Ser Ser Val Glu Glu Leu
                165                 170                 175

Phe Ser Asp Val Asp Ser Ser Tyr Tyr Asp Leu Asp Thr Val Leu Thr
            180                 185                 190

Gly Met Met Ser Gly Thr Lys Ser Ser Leu Cys Asn Gly Leu Glu Gly
        195                 200                 205

Phe Ala Ala Thr Pro Pro Pro Ser Ser Thr Cys Lys Ser Asp Leu
    210                 215                 220

Ala Glu Leu Asp His Val Val Glu Ile Leu Val Glu Thr
225                 230                 235
```

<210> SEQ ID NO 3
<211> LENGTH: 2082
<212> TYPE: DNA
<213> ORGANISM: Homo sapiens
<220> FEATURE:
<221> NAME/KEY: CDS
<222> LOCATION: (75)..(797)

<400> SEQUENCE: 3

```
gggaagctgg cggcacagcc gtggcgcctg gctgagcaga ggacccggcg gcggcctcg    60 cgggtcagga caca atg ttt gca cga gga ctg aag agg aaa tgt gtt ggc   110
               Met Phe Ala Arg Gly Leu Lys Arg Lys Cys Val Gly
                 1               5                  10 cac gag gaa gac gtg gag gga gcc ctg gcc ggc ttg aag aca gtg tcc   158
His Glu Glu Asp Val Glu Gly Ala Leu Ala Gly Leu Lys Thr Val Ser
             15                  20                  25 tca tac agc ctg cag cgg cag tcg ctc ctg gac atg tct ctg gtg aag   206
Ser Tyr Ser Leu Gln Arg Gln Ser Leu Leu Asp Met Ser Leu Val Lys
         30                  35                  40
```

| | | |
|---|---|---|
| ttg cag ctt tgc cac atg ctt gtg gag ccc aac ctg tgc cgc tca gtc<br>Leu Gln Leu Cys His Met Leu Val Glu Pro Asn Leu Cys Arg Ser Val<br>45                        50                       55                   60 | 254 |
| ctc att gcc aac acg gtc cgg cag atc caa gag gag atg acg cag gat<br>Leu Ile Ala Asn Thr Val Arg Gln Ile Gln Glu Glu Met Thr Gln Asp<br>                     65                      70                    75 | 302 |
| ggg acg tgg cgc aca gtg gca ccc cag gct gca gag cgg gcg ccg ctc<br>Gly Thr Trp Arg Thr Val Ala Pro Gln Ala Ala Glu Arg Ala Pro Leu<br>              80                      85                     90 | 350 |
| gac cgc ttg gtc tcc acg gag atc ctg tgc cgt gca gcg tgg ggg caa<br>Asp Arg Leu Val Ser Thr Glu Ile Leu Cys Arg Ala Ala Trp Gly Gln<br>                 95                     100                 105 | 398 |
| gag ggg gca cat cct gct cct ggc ttg ggg gac ggc cac aca cag ggt<br>Glu Gly Ala His Pro Ala Pro Gly Leu Gly Asp Gly His Thr Gln Gly<br>110                       115                     120 | 446 |
| cca gtt tct gac ctt tgc cca gtc acc tca gca cag gca cca agg cac<br>Pro Val Ser Asp Leu Cys Pro Val Thr Ser Ala Gln Ala Pro Arg His<br>125                       130                     135                 140 | 494 |
| ctg cag agc agc gcc tgg gag atg gat ggc cct cga gaa aac aga gga<br>Leu Gln Ser Ser Ala Trp Glu Met Asp Gly Pro Arg Glu Asn Arg Gly<br>                 145                     150                 155 | 542 |
| agc ttt cac aag tca ctt gat cag ata ttt gaa acg ctg gag act aaa<br>Ser Phe His Lys Ser Leu Asp Gln Ile Phe Glu Thr Leu Glu Thr Lys<br>           160                     165                    170 | 590 |
| aac ccc agc tgc atg gaa gag ctg ttc tca gac gtg gac agc ccc tac<br>Asn Pro Ser Cys Met Glu Glu Leu Phe Ser Asp Val Asp Ser Pro Tyr<br>                 175                     180                 185 | 638 |
| tac gac ctg gac aca gta ctg aca ggc atg atg ggg ggt gcc agg ccg<br>Tyr Asp Leu Asp Thr Val Leu Thr Gly Met Met Gly Gly Ala Arg Pro<br>           190                     195                    200 | 686 |
| ggc ccc tgc gaa ggg ctc gag ggc ttg gct ccg gcc acc cca ggc cct<br>Gly Pro Cys Glu Gly Leu Glu Gly Leu Ala Pro Ala Thr Pro Gly Pro<br>205                       210                     215                 220 | 734 |
| agc tcc agc tgc aag tcc gac ctg ggc gag ctg gac cac gtg gtg gag<br>Ser Ser Ser Cys Lys Ser Asp Leu Gly Glu Leu Asp His Val Val Glu<br>                 225                     230                 235 | 782 |
| atc ctg gtg gag acc tgagcaggag ccctgagtgc tcacagccgc ctctgacgca<br>Ile Leu Val Glu Thr<br>           240 | 837 |
| ttgacacgtg agcactggct cccacggagg gtgcgcctgc cgccagcggc ccagccttgc | 897 |
| tgccctgtct gctgattctg agaaatccca gaacagccca ttaccagtgg ggctgcagcc | 957 |
| ctaggcccgt cccactcacc tcccccctgt ggagcgccag gcagaggctg ttctggaagg | 1017 |
| cttcttgtct tctgacgtcc ccacagccct gggcccctcg tgtctctttg tgtccccac | 1077 |
| tgtagaggac ggtgagccgc agctgcatca acctcctttt acctttagat aggtgaattt | 1137 |
| ttacaattca gttttacatg ttttgggcag tattttgtct aagatatat ttttaaact | 1197 |
| ttttatacct tatctcttta gattttttca gctattttct taaaagtata ttttttctat | 1257 |
| aaacatcctt tgctgctaca ttagaacttt tatagcctaa acaattgcag ttggtgtgtt | 1317 |
| tcatttttt aaggtttaaa taagggtttt ttgtttttgtt ttgtttttg cagtgagcat | 1377 |
| cactacagtc tcagtcaaca gtgtgaatgt atcatgtttt actttaaatg tgtgtgtgat | 1437 |
| acttcttcat tatgtcctgc gctgcagtga gacctgggtg aaaatcagga gccgcacaca | 1497 |
| gccacatctt cctagaccta agagtaaatt atggaggatt ttatttatgt ctatttatat | 1557 |
| gtaaatgtca ttgaagacaa aggtcaaata tttgtctgtt tgtagatcac aggcaccagt | 1617 |

-continued

```
tggtcttcag ggacctcata gcccctcggt ggtgccttct caaggcagtg ttcctggagg    1677
ctcccatcag ggtcagccca tgcacctgcc ctgggtgagg aagtagcatt gctgctggat    1737
gagaaacgcc tgcgctgctc tgttagactg gtgctgaaac aaaaggttaa ggctaggttg    1797
aagtctagaa tgaaagaaat ctgaatccat gtcattcata accccttgat ctgtagtgtc    1857
atgggtgctg ccgcaggcag ggagtgagct gggggtgcct gcagccttcc actcctgccc    1917
cgcctcaccc cacatgctcc ctgtttctca tgctttctct aacttcctca cccttaacc    1977 aaaaaggtgt gttttctttt gtgcatatag ccattcttaa atatcagtga tgtaaacctc    2037
actttattaa aaaattatcc agcaaaaaaa aaaaaaaaaa aaaaa                    2082
```

<210> SEQ ID NO 4
<211> LENGTH: 241
<212> TYPE: PRT
<213> ORGANISM: Homo sapiens

<400> SEQUENCE: 4

```
Met Phe Ala Arg Gly Leu Lys Arg Lys Cys Val Gly His Glu Glu Asp
1               5                   10                  15

Val Glu Gly Ala Leu Ala Gly Leu Lys Thr Val Ser Ser Tyr Ser Leu
            20                  25                  30

Gln Arg Gln Ser Leu Leu Asp Met Ser Leu Val Lys Leu Gln Leu Cys
        35                  40                  45

His Met Leu Val Glu Pro Asn Leu Cys Arg Ser Val Leu Ile Ala Asn
    50                  55                  60

Thr Val Arg Gln Ile Gln Glu Glu Met Thr Gln Asp Gly Thr Trp Arg
65                  70                  75                  80

Thr Val Ala Pro Gln Ala Ala Glu Arg Ala Pro Leu Asp Arg Leu Val
                85                  90                  95

Ser Thr Glu Ile Leu Cys Arg Ala Ala Trp Gly Gln Glu Gly Ala His
            100                 105                 110

Pro Ala Pro Gly Leu Gly Asp Gly His Thr Gln Gly Pro Val Ser Asp
        115                 120                 125

Leu Cys Pro Val Thr Ser Ala Gln Ala Pro Arg His Leu Gln Ser Ser
    130                 135                 140

Ala Trp Glu Met Asp Gly Pro Arg Glu Asn Arg Gly Ser Phe His Lys
145                 150                 155                 160

Ser Leu Asp Gln Ile Phe Glu Thr Leu Glu Thr Lys Asn Pro Ser Cys
                165                 170                 175

Met Glu Glu Leu Phe Ser Asp Val Asp Ser Pro Tyr Tyr Asp Leu Asp
            180                 185                 190

Thr Val Leu Thr Gly Met Met Gly Gly Ala Arg Pro Gly Pro Cys Glu
        195                 200                 205

Gly Leu Glu Gly Leu Ala Pro Ala Thr Pro Gly Pro Ser Ser Ser Cys
    210                 215                 220

Lys Ser Asp Leu Gly Glu Leu Asp His Val Val Glu Ile Leu Val Glu
225                 230                 235                 240

Thr
```

<210> SEQ ID NO 5
<211> LENGTH: 106
<212> TYPE: PRT
<213> ORGANISM: Danio rerio

<400> SEQUENCE: 5

```
Met Phe Ser Lys Gly Thr Lys Arg Lys Phe Ala Asp Gly Gly Glu Glu
1               5                   10                  15

Ile Ser Asp Asp Gly Leu Val Ala Ala Arg Val Ala Ser Ser Tyr Ser
            20                  25                  30

Leu Gln Arg Gln Ser Leu Leu Asp Met Ser Leu Ile Lys Leu Gln Leu
        35                  40                  45

Cys His Met Leu Val Glu Pro Asn Leu Cys Arg Ser Val Leu Ile Ala
    50                  55                  60

Asn Thr Val Arg Gln Ile Gln Glu Glu Met Thr His Asp Gly Ser Trp
65                  70                  75                  80

His Met Val Thr Glu Ala Phe Cys Gly Ala Ser Gln Ser Pro Ser Glu
                85                  90                  95

Arg Leu Val Ala Thr Glu Val Leu Cys Arg
            100                 105
```

<210> SEQ ID NO 6
<211> LENGTH: 113
<212> TYPE: PRT
<213> ORGANISM: Mus musculus

<400> SEQUENCE: 6

```
Met Phe Ala Arg Gly Leu Lys Arg Lys Tyr Gly Asp Gln Glu Glu Gly
1               5                   10                  15

Val Glu Gly Phe Gly Thr Val Pro Ser Tyr Ser Leu Gln Arg Gln Ser
            20                  25                  30

Leu Leu Asp Met Ser Leu Val Lys Leu Gln Leu Cys His Met Leu Val
        35                  40                  45

Glu Pro Asn Leu Cys Arg Ser Val Leu Ile Ala Asn Thr Val Arg Gln
    50                  55                  60

Ile Gln Glu Glu Met Ser Gln Asp Gly Val Trp His Gly Met Ala Pro
65                  70                  75                  80

Gln Asn Val Asp Arg Ala Pro Val Glu Arg Leu Val Ser Thr Glu Ile
                85                  90                  95

Leu Cys Arg Thr Val Arg Gly Ala Glu Glu His Pro Ala Pro Glu
            100                 105                 110

Leu
```

<210> SEQ ID NO 7
<211> LENGTH: 117
<212> TYPE: PRT
<213> ORGANISM: Homo sapiens

<400> SEQUENCE: 7

```
Met Phe Ala Arg Gly Leu Lys Arg Lys Cys Val Gly His Glu Glu Asp
1               5                   10                  15

Val Glu Gly Ala Leu Ala Gly Leu Lys Thr Val Ser Ser Tyr Ser Leu
            20                  25                  30

Gln Arg Gln Ser Leu Leu Asp Met Ser Leu Val Lys Leu Gln Leu Cys
        35                  40                  45

His Met Leu Val Glu Pro Asn Leu Cys Arg Ser Val Leu Ile Ala Asn
    50                  55                  60

Thr Val Arg Gln Ile Gln Glu Glu Met Thr Gln Asp Gly Thr Trp Arg
65                  70                  75                  80

Thr Val Ala Pro Gln Ala Ala Glu Arg Ala Pro Leu Asp Arg Leu Val
                85                  90                  95

Ser Thr Glu Ile Leu Cys Arg Ala Ala Trp Gly Gln Glu Gly Ala His
```

```
                100              105                110
Pro Ala Pro Gly Leu
        115

<210> SEQ ID NO 8
<211> LENGTH: 20
<212> TYPE: DNA
<213> ORGANISM: synthetic construct

<400> SEQUENCE: 8
cgaaggagtg gcggggtctg                                                    20

<210> SEQ ID NO 9
<211> LENGTH: 20
<212> TYPE: DNA
<213> ORGANISM: synthetic construct

<400> SEQUENCE: 9
ttcctttgcc ctcgtgctga                                                    20

<210> SEQ ID NO 10
<211> LENGTH: 20
<212> TYPE: DNA
<213> ORGANISM: synthetic construct

<400> SEQUENCE: 10
gttgagagat catctccacc                                                    20

<210> SEQ ID NO 11
<211> LENGTH: 20
<212> TYPE: DNA
<213> ORGANISM: synthetic construct

<400> SEQUENCE: 11
agcgatgatg aaccaggtta                                                    20
```

HEPP, A NOVEL GENE WITH A ROLE IN HEMATOPOIETIC AND NEURAL DEVELOPMENT

This application claims priority to U.S. application No. 60/268,923, filed Feb. 16, 2001, which is incorporated herein by reference.

FIELD OF THE INVENTION

The invention relates to a novel conserved gene and protein product, designated Hepp (hematopoietic progenitor protein, that has a role in mammalian hematopoiesis and neural function.

BACKGROUND INFORMATION

The life-long maintenance and regenerative capacity of the hematopoietic system depends upon self-renewal and differentiation of pluripotent hematopoietic stem cells (HSC). The HSC give rise to all mature blood cell types by differentiating through intermediate progenitor cells that undergo lineage commitment and subsequent development along a single pathway (1–5). During the last two decades a highly complex regulatory network of molecular mechanisms, necessary to control lineage commitment and differentiation of blood cells has been identified, including growth factors and receptors, cell-cell interaction molecules, signal transduction molecules and transcription factors (6–15). Due to distinct functional features of HSC, progenitors and mature blood cells, it is reasonable to assume that these properties are regulated at least in part by molecules that are preferentially expressed at particular stages of blood cell development. One approach to identify molecules that are important for self-renewal and lineage commitment of HSC and progenitors is to focus on rare populations of cells that are enriched for HSC and progenitors. Construction of HSC and progenitor cell-specific subtracted cDNA libraries, coupled with cDNA sequencing and microarray-based studies of gene expression patterns, will be necessary to molecularly define self-renewal, functional pluripotency and lineage commitment of HSC and progenitors and to elucidate the extraordinary developmental plasticity of HSC (16–19). Using subtracted cDNA libraries and cDNA microarray approach Phillips et al. (17) have recently reported results of a genomewide gene expression analysis in mouse fetal liver HSC and progenitors. The complete data in the form of a database represent the first step in elucidating the molecular phenotype of hematopoietic stem cells and progenitors.

Elucidation of the differential gene expression during differentiation of hematopoietic stem cell and progenitors should have far reaching implications for ex vivo manipulation of HSC, clinical bone marrow transplantation and gene therapy of hematological disorders.

To identify novel molecules involved in intrinsic regulation of HSC and progenitor cell lineage commitment and differentiation we have generated full-length and subtracted cDNA libraries from mouse adult bone marrow cell populations enriched for HSC (Lin$^-$Sca-1$^+$ cells) and progenitors (Lin$^-$Sca-1$^-$ cells) (19). Phenotypically and functionally defined population of primitive Lin$^-$Sca-1$^+$ cells comprises 0.1–0.2% of bone marrow cells and contains virtually all HSC and primitive progenitors, whereas more differentiated Lin$^-$Sca-1$^-$ cells contain committed progenitors but lack HSC. Here we describe cloning and characterization of a novel gene, Hepp, that is expressed preferentially in mouse fetal and adult hematopoietic progenitors and mature blood cells.

Certain aspects of the present invention have been disclosed in Abdullah et al. (19).

SUMMARY OF THE INVENTION

Through differential screening of mouse hematopoietic stem cells (HSC) and progenitor substracted cDNA libraries, we have identified a progenitor cell-specific transcript that represents a novel conserved gene, designated Hepp (hematopoietic progenitor protein). Mouse and human Hepp genes encode proteins of 267 and 241 amino acids with no detectable known functional domains or motifs. The mouse gene and corresponding protein are set forth in SEQ ID NO:1 and SEQ ID NO:2, respectively. The human gene and corresponding protein are set forth in SEQ ID NO:3 and SEQ ID NO:4, respectively. During embryonic hematopoiesis Hepp is not expressed in mouse fetal liver HSC (Sca-1$^+$ c-kit$^+$ AA4.1$^+$Lin$^-$ cells), but is abundantly transcribed in populations of hemotopoietic progenitors (AA4.1$^-$). In adult mice, Hepp is not transcribed in highly enriched populations of bone marrow HSC (Rh$^-$123$^{low}$Sca-1$^+$c-kit$^+$Lin$^-$ cells), but its expression is unregulated as more heterogeneous population of bone marrow HSC (Lin$^-$Sca-1$^+$ cells) differentiates into progenitors (Lin$^-$Sca-1$^-$ cells) and more mature lymphoid and myeloid cell types. The human gene was localized to chromosome 14q32, a region with frequent chromosome aberrations associated with multiple cases of acute myeloid leukemia, chronic lymphoproliferative disorder, acute lymphoblastic leukemia, non-Hodgkin's lymphoma, and myelodysplastic syndrome, for which the genes involved are unknown. Evolutionary conservation and differential expression in fetal and adult HSC and progenitors suggest that Hepp gene could play an important role in HSC/progenitor cell lineage commitment and differentiation, and could be involved in etiology of hematological malignancies.

The gene and associated protein should be useful in a variety of contexts, for example, as reagents for differential identification of the tissue(s) or cell type(s) present in a biological sample and for diagnosis of diseases and conditions which include, but are not limited to, neural disorders and malignancies, particularly malignancies of the blood. Polypeptides of the invention and antibodies directed to these polypeptides are expected to be useful in providing immunological probes for differential identification of the tissue(s) or cell type(s), by means familiar to persons of skill in the art. For a number of disorders of neural and hematological tissues or cells, particularly of the nervous system and blood, expression of the Hepp gene at significantly higher or lower levels may be routinely detected in certain tissues or cell types relative to the standard gene expression level, i.e., the expression level in healthy tissue or bodily fluid from an individual not having the disorder.

The tissue distribution of Hepp gene expression, and the characteristics of the Hepp knock-out mouse described herein, indicate that polynucleotides and polypeptides corresponding to this gene are useful for the detection, treatment, and/or prevention of neurodegenerative disease states, such as, for example, amyotrophic lateral sclerosis, and hematological disorders, particularly neoplasms of the blood such as acute myelomonocytic leukemia, lymphoblastic lymphoma, chronic lymphocytic leukemia, acute lymphoblastic leukemia, multiple myeloma, B-prolymphocytic leukemia, plasma cell leukemia, adult T-cell lymphoma/leukemia, diffuse large B-cell lymphoma, nodal marginal zone B-cell lymphoma, Burkitt's lymphoma, follicular lymphoma, hairy cell leukemia, mantle cell lymphoma, splenic marginal zone B-cell lymphoma, and T-prolymphocytic leukemia.

The terms "nucleic acid" "oligonucleotide", and "polynucleotide" are intended to include RNA, DNA, or RNA/DNA hybrid sequences of more than one nucleotide in either single chain or duplex form, and are used interchangeably herein.

The terms "peptide", "polypeptide" and "protein", as used herein, refer to a sequence of naturally occurring amino acids, more particularly to a translated amino acid sequence generated from a polynucleotide of the invention. The proteins of the invention may in some instances have undergone postranslational modification. In general, "peptide" refers to a sequence of less than 10 residues, "polypeptide" refers to a sequence of 10 or more amino acid residues and as used herein is intended to encompass proteins as well.

The terms "complementary" or "complement thereof", as used herein, refer to sequences of polynucleotides which are capable of forming Watson & Crick base pairing with another specified polynucleotide throughout the entirety of the complementary region. This term is applied to pairs of polynucleotides based solely upon their sequences and does not refer to any specific conditions under which the two polynucleotides would actually bind.

For the purposes of this invention, when referring to nucleic acid and polypeptide sequences, percent similarity and percent identity are calculated according to the methods of CLUSTAL W (32).

As used herein, the term "isolated" refers to material removed from its original environment (e.g., for naturally occurring substances, removed from their natural environment). Such material could be part of a vector or a composition of matter, or could be contained within a cell, if said vector, composition or cell is not the original environment of the material.

As used herein, the term "transgenic animal" is an animal containing a defined change to its germ line, wherein the change is not ordinarily found in the wild-type animal and can be passed on to the animal's progeny. The change to the animal's germ line can be an insertion, a substitution, or a deletion. In a broad sense, the term "transgenic" encompasses organisms where a gene has been eliminated or disrupted so as to result in the elimination of a phenotype associated with the disrupted gene ("knock-out (KO) animals"). The term "transgenic" also encompasses organisms containing modifications to their existing genes and organisms modified to contain exogenous genes introduced into their germ line.

It is one object of the invention to provide an isolated nucleic acid comprising a sequence that is at least 70% identical to SEQ ID NO: 1 or SEQ ID NO:3, or a sequence that is complementary thereto. Preferably the sequence is at least 77% identical, more preferably 80% identical, and even more preferably 85%, 90%, 95%, 98%, 99% or 100% identical to SEQ ID NO:1 or SEQ ID NO:3.

The invention also provides an isolated nucleic acid comprising a sequence that is at least 70% identical to a fragment of SEQ ID NO:1 or SEQ ID NO:3, the fragment representing at least 50 contiguous bases, preferably 100 contiguous bases and most preferably 150 contiguous bases of SEQ ID NO:1 or SEQ ID NO:3. Preferably the sequence is at least 77% identical, more preferably 80% identical, and even more preferably 85%, 90%, 95%, or 100% identical to said contiguous bases.

The nucleic acids of the invention may be produced recombinantly, synthetically, or by any means available to those of skill in the art, and may be cloned using techniques known in the art. In this regard, the invention also includes a vector comprising the nucleic acid of the invention, and a host cell comprising the nucleic acid of the invention.

The invention also provides a polypeptide or protein comprising an amino acid sequence that is at least 70% identical to SEQ ID NO:2, SEQ ID NO:4, SEQ ID NO:5, SEQ ID NO:6, or SEQ ID NO:7. Preferably the sequence is at least 75% identical, more preferably 80% identical, and even more preferably 85%, 90%, 95%, 98%, 99% or 100% identical to one of SEQ ID NO:2, SEQ ID NO:4, SEQ ID NO:5, SEQ ID NO:6, or SEQ ID NO:7. In an alternate embodiment, the amino acid sequence is at least 60%, preferably 70%, 75%, 80%, and more preferably 85%, 90%, 95%, 98%, 99% or 100% similar to SEQ ID NO:2, SEQ ID NO:4, SEQ ID NO:5, SEQ ID NO:6, or SEQ ID NO:7.

The invention also provides an isolated polypeptide or protein comprising a sequence that is at least 70% identical to a fragment of SEQ ID NO:2, SEQ ID NO:4, SEQ ID NO:5, SEQ ID NO:6, or SEQ ID NO:7, the fragment representing at least 10 contiguous amino acid residues, preferably 20 contiguous amino acid residues and most preferably 50 contiguous residues of SEQ ID NO:2, SEQ ID NO:4, SEQ ID NO:5, SEQ ID NO:6, or SEQ ID NO:7. Preferably the sequence is at least 75% identical, more preferably 80% identical, and even more preferably 85%, 90%, 95%, 98%, 99% or 100% identical to said contiguous residues.

The polypeptide of the present invention may be produced by conventional methods of chemical synthesis or by recombinant DNA techniques. For example, a host microorganism may be transformed with a DNA fragment encoding the polypeptide and the polypeptide harvested from the culture. The host organism may be, for example, a bacterium, a yeast or a mammalian cell, whereby the DNA fragment in question is integrated in the genome of the host organism or inserted into a suitable expression vector capable of replicating in the host organism. The DNA fragment is placed under the control of regions containing suitable transcription and translation signals. Methods for obtaining polypeptides by these means are familiar to persons skilled in the art.

The invention also provides a non-human mutant vertebrate, or "knock-out (KO) animal" in which the Hepp gene has been impaired at one or both loci in somatic and germ cells. A "knock-out animal" is an animal in which selected genes have been mutated to prevent expression of functional protein products. In this regard, the invention provides a non-human mutant vertebrate, in which all or some of the germ and somatic cells contain a mutation in at least one Hepp locus, which mutation is introduced into the vertebrate, or an ancestor of the vertebrate, at an embryonic stage. The term "vertebrate" encompasses mammals, birds, reptiles, amphibians, and fishes that possess a Hepp gene or equivalent. Preferably the vertebrate is a non-human mammal, most preferably a mouse, rat, or rabbit.

In one preferred embodiment, the mutation produces a phenotype in a mammal characterized by perturbed hematopoiesis consisting of bone marrow cytopenia, overproduction and/or accumulation of hematopoietic progenitors, and splenomegaly with follicular hyperplasia. In an especially preferred embodiment, the vertebrate is a mouse that is heterozygous or homozygous for HEPP⁻, a knock-out gene that results in a reduction or absence of functional HEPP protein. Such mice can be obtained by treating mouse embryos with ES cell clone KST303. Other means of producing mutant animals, such as knock-in techniques, are familiar to those of skill in the art.

The invention also provides a means of producing a KO mammal, in particular a mouse, that is heterozygous or homozygous for a defective Hepp gene (e.g. Hepp−). In one method of producing the transgenic animals, transformed ES cells containing a disrupted Hepp gene having undergone homologous recombination, are introduced into a normal blastocyst. The blastocyst is then transferred into the uterus of a pseudo-pregnant female for gestation and delivery. Resulting heterozygous mutant animals are then bred to obtain homozygous mutant animals. Other means of producing KO animals are familiar to those of skill in the art. Examples are disclosed in U.S. Pat. No. 6,015,676 (Lin et al.) and Gene Knockout Protocols. In: Methods in Molecular Biology, vol. 158, 2001. Edited by: M. J. Tymms and I. Kola. Humana Press, Totowa, N.J., incorporated herein by reference.

The mutant vertebrate of the invention may be one in which all of the germ and somatic cells contain the mutation, i.e., the vertebrate is either a heterozygote or a homozygote for the mutation. The vertebrate may be one wherein both of the Hepp alleles in all of the germ and somatic cells contain the mutation, i.e., the vertebrate is a homozygote for the mutation. Alternatively, the vertebrate may be a chimera (an animal in which only some of the germ and somatic cells contain the mutation).

The mutant vertebrate of the invention should be useful, inter alia, in screening drugs for the treatment of neurodegenerative disorders such as amyotrophic lateral sclerosis (ALS) and testing of novel hematopoietic cytokines/growth factors for mobilization and differentiation of stem and progenitor cells.

BRIEF DESCRIPTION OF THE DRAWINGS

FIG. 1A. Complementary DNA sequence (SEQ ID NO:1) and deduced amino acid sequence (SEQ ID NO:2) for the mouse Hepp gene. The 5' in-frame stop codon found upstream of the start codon is underlined in the nucleotide sequence. The stop codon is indicated by an asterisk. The polyadenylation signal-like sequence is underlined in bold. The nucleotide sequence data reported here appear in the GenBank nucleotide sequence databases under Accession No. AF322238.

FIG. 1B. Complementary DNA sequence (SEQ ID NO:3) and deduced amino acid sequence (SEQ ID NO:4) for the human HEPP gene. The 5' in-frame stop codon found upstream of the start codon is underlined in the nucleotide sequence. The stop codon is indicated by an asterisk. The polyadenylation signal-like sequence is underlined in bold. The nucleotide sequence data reported here appear in the GenBank nucleotide sequence databases under Accession No. 322239.

FIG. 2. ClustalW amino acid sequence alignment of the mouse (SEQ ID NO: 2) and human (SEQ ID NO:4) HEPP proteins.

FIG. 3. Amino acid sequence alignment of the N terminal portion of zebrafish (SEQ ID NO:5), mouse (SEQ ID NO:6) and human (SEQ ID NO:7) HEPP proteins.

FIG. 5. Semiquantitative duplex PCR and RT-PCR expression analysis of Hepp and HPRT (control) in mouse fetal liver and adult bone marrow HSC and progenitor cell populations.

FIG. 6. Semiquantitative duplex RT-PCR expression analysis of Hepp and HPRT in various hematopoietic cell lines demonstrates that mouse Hepp is ubiquitously expressed in different stages of lymphoid and myeloid cell development.

DETAILED DESCRIPTION OF THE INVENTION

Materials and Methods

Figure 4A:
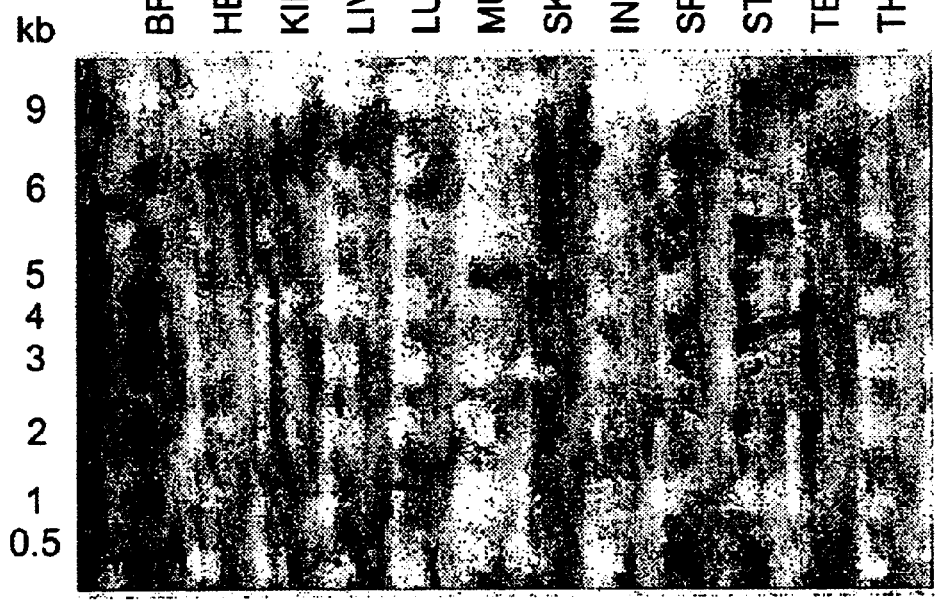
FIG. 4. Northern analysis of Hepp expression in adult mouse tissues. (a) Hepp is transcribed at a very low level in heart, lung, spleen, and thymus and at a higher level in muscle. (b) Hybridization with actin probe as a positive control.

Fluorescence-Activated Sorting of Mouse Hematopoietic Stem and Progenitor Cells.

Phenotypically and functionally defined populations of primitive Lin−Sca-1+ cells (comprising 0.1–0.2% of bone marrow cells and containing virtually all HSC and primitive progenitors) and more differentiated Lin−Sca-1− cells (containing committed progenitors but lacking HSC) (20–23) were isolated from the bone marrow of 6- to 8-week-old C57BL/6J mice (Taconic, Germantown, N.Y.). Cell sorting was conducted as described previously (21), using the FACStar Vantage flow cytometer (Becton-Dickinson Immunocytometry Systems, San Jose, Calif.).

Library Construction and Subtractive Hybridization

Poly(A)+ RNA (0.5 μg) was isolated from sorted Lin−Sca-1+ and Lin−Sca-1− cells using Micro-FastTrack MRNA isolation procedure (Invitrogen). Full-length Lin−Sca-1+ and Lin−Sca-1− cell-specific cDNA libraries were constructed in λZAPII vector using CapFinder cDNA library construction method, according to manufacturer's protocol (Clontech, Palo Alto, Calif., USA). Lin−$^{Sca-}$1+ (titer 4.8×10$^{10}$ pfu/ml) and Lin−Sca-1− (titer 5.6×10$^{10}$ pfu/ml) cell-specific libraries were arrayed (2×10$^6$ clones) into a 96-well format for efficient PCR-based screening (24). Lin−Sca-1+ and Lin−Sca-1− cell-specific subtracted cDNA libraries were constructed by suppression subtractive hybridization (25, 26) using a PCR-Select kit (Clontech). Double-stranded cDNAs were synthesized from mouse Lin−Sca-1+ and Lin−Sca-1− bone marrow cell poly(A)+RNA, digested with RsaI, and used as both tester and driver in reciprocal subtractive hybridization. After two rounds of hybridization portions of reactions were subjected to two rounds of PCR to selectively amplify differentially expressed cDNAs, which were cloned into pGEM-T vector (Promega, Madison, Wis.). Individual clones from subtracted cDNA libraries were arrayed as dot blots in a 96-well format and hybridized with labeled probes derived from tester and driver cDNAs (19). Confirmed differentially expressed cDNA clones were sequenced and analyzed using computer-assisted search of GenBank/ EMBL and UniGene databases (www.ncbi.nlm.nih.gov/ UniGene/index.html).

Cloning and Sequence Analysis of Hepp cDNA

Mouse cDNA for Hepp was isolated by PCRbased screening of arrayed full-length Lin2Sca-12 cell-specific cDNA library (24). The longest isolated clones were sequenced and derived Hepp cDNA was analyzed using the nonredundant and EST division of the GenBank database, UniGene database, and SMART (Simple Modular Architecture Research Tool, http://smart.embl-heidelberg.de/). Proteome WormPD database (http://www.proteome.com/databases) and DRES (Drosophila Related Expressed Sequences) Search Engine (http://hercules.tigem.it/DRES/dres.html) (27) were used to identify Caenorhabditis elegans and Drosophila orthologs of Hepp.

Expression Analysis

Mouse multiple tissue Northern blot was purchased from OriGene Technologies Inc. (Rockville, Md.). In vitro transcribed partial Hepp cDNA was labeled with North2South HRP Direct labeling kit (PIERCE, Rockford, Ill.) and used as a nonradioactive probe. Blot was prehybridized (30 min) and hybridized (1 h) at 55° C., washed according to manufacturer's instructions, and exposed to X-ray film (Kodak) using Du Pont intensifying screens. Hybridization with non-radioactively labeled actin probe was used as a positive control.

Expression in mouse fetal and adult HSC and progenitor cell populations was analyzed by (a) semiquantitative PCR screening of cDNA libraries from fetal liver HSC (Sca-1$^+$c-kit$^+$AA4.1$^+$Lin$^-$ cells), fetal liver progenitors and mature blood cells (AA4.1$^-$), and adult bone marrow HSC (Rh-123$^{low}$Sca-1$^+$c-kit$^+$Lin$^-$ cells), and (b) semiquantitative reverse transcription PCR (RT-PCR) using first strand cDNAs prepared from sorted Lin$^-$Sca-1$^+$and Lin$^-$Sca-1$^-$ bone marrow cells according to the manufacturer's protocol (Clontech). Sca-1$^+$c-kit$^+$AA4.1$^+$Lin$^-$, AA4.1$^-$, and Rh-123$^{low}$Sca-1$^+$c-kit$^+$Lin$^-$ cell-specific cDNA libraries (prepared by Clontech's CapFinder cDNA library construction method) were a kind gift from Dr. Ihor Lemischka (Princeton University).

Both PCR and RT-PCRs were performed in duplex using different dilutions of cDNA libraries and first strand cDNAs, with mouse Hepp primers amplifying a 446-bp fragment (5' oligo 5'-CGAAGGAGTGGCGGGGTCTG-3' [SEQ ID NO:8]; 3' oligo 5'-TTCCTTTGCCCTCGTGCTGA-3' [SEQ ID NO:9]), and primers for hypoxanthine-guanine-phosphorybosyltransferase (HPRT) (5' oligo 5'-GTTGAGAGATCATCTCCACC-3' [SEQ ID NO:10]; 3' oligo 5'-AGCGATGATGAACCAGGTTA-3' [SEQ ID NO:11]) which amplify a 340-bp fragment as an internal positive control. Reactions were performed in an Eppendorf Mastercyler for 25–40 cycles (95° C. for 30 s, 57° C. for 45 s, 72° C. for 30 s) various hematopoietic lineages was also assessed by semiquantitative duplex RT-PCR. A panel of the following lineagespecific mouse hematopoietic cell lines was used: LyD9 (pluripotent progenitor cell line), FDC-P1 (myeloid progenitor cell line), 1881 (pro-B cell line), BaF/3 and 70Z/3 (pre-B cell lines), CH33 and M12 (B cell lines), NFS-70 (pro-B cell lymphoma), NFS-5 (pre-B cell lymphoma), A20 and WEHI-279 (B cell lymphoma lines), J558 (B cell myeloma), EL4 and WEHI 7.1 (T cell lymphoma), WEHI-3B (myelomonocytic cell line), and RAW 309 and J774A.1 (monocyte-macrophage cell lines). These cell lines can be obtained from the American Type Culture Collection (ATCC) Manassas, Va. 20108. Total RNA (2 $\mu$g) from each cell line was reverse transcribed using random hexamers (Pharmacia, Piscataway, N.J.) and MMLV reverse transcriptase (GIBCO) in a 20-$\mu$l reaction, and 2 $\mu$l of the first-strand cDNA was used as a template in a duplex PCR (30 cycles; 95° C. for 30 s, 57° C. for 45 s, 72° C. for 30 s) with primers for Hepp and HPRT.

Results

Isolation and Analysis of Full-Length cDNA for Hepp

After differential screening of subtracted Lin$^-$Sca-1$^+$ and Lin$^-$Sca-1$^-$ cell-specific libraries, differentially expressed cDNA clones were subjected to automated sequencing and computer assisted analysis. BLAST search of the GenBank/ EMBL database identified one of the ESTs (LS215), isolated from Lin$^-$Sca-1$^-$ cell-specific subtracted cDNA library, as a novel gene. Based on the preferential expression in adult bone marrow progenitors the gene was designated Hepp for hematopoietic progenitor protein. Mouse cDNA clone for Hepp was isolated by PCR-based screening of arrayed full-length Lin$^-$Sca-1$^-$ cell specific cDNA library using sequence-specific primers. The two longest isolated clones were sequenced and analyzed. Mouse Hepp transcript (2082 bp) contains an open reading frame (ORF) of 711 bp with one in-frame stop codon upstream of the first ATG codon, and encodes a protein of 237 amino acids (theoretical Mr 26.1 kDa) with no known domains or motifs (Accession No. AF322238) (FIG. 1A). In the UniGene database mouse Hepp cDNA is represented by one cluster of uncharacterized ESTs (Mm.28595). Search of the human EST division of the GenBank database with the mouse Hepp cDNA sequence identified several homologous ESTs, that are identical to human FLJ20764 cDNA (Accession No. AK000771) of unknown function. FLJ20764 cDNA (1918 bp) contains partial ORF (609 bp) that encodes a 202 amino acid protein similar to mouse Hepp protein and is represented by one cluster of uncharacterized ESTs Hs.34045) in the UniGene database. According to the NCBI HomoloGene (www.ncbi.nlm.nih.gov/HomoloGene/, a homology resource which includes both curated and calculated orthologs and homologs for human, mouse, rat, zebrafish, cow and fly genes represented in the UniGene), mouse ESTs from UniGene cluster Mm.28595 and human hypothetical protein FLJ20764, represented by the UniGene cluster Hs.34045, are calculated orthologs with 88% sequence identity. All human ESTs from cluster Hs.34045 were assembled into a single contig with EST Assembly Machine (http://gcg.tigem.it/cgi-bin/uniestass.pl), conceptually translated in all six frames (http://dot.imgen.bcm.tmc.edu:9331/ seq-util/seq-util.html) and compared with nucleotide and amino acid sequence of mouse Hepp and human FLJ20764 cDNA. Electronically extended cDNA (2082 bp) for human FLJ20764 contains an ORF of 723 bp with one in-frame stop codon upstream of the first ATG codon and encodes a 241 amino acid protein (theoretical Mr 26.1 kDa) (Accession No. AF322239) (FIG. 1B). ClustalW amino acid sequence alignment (32) has shown that mouse Hepp and human FLJ20764 proteins share 73% identity and 77% similarity, with several highly conserved contiguous blocks of amino acids (FIG. 2), again indicating that FLJ20764 gene most likely represents the human ortholog of the mouse Hepp gene. Based on SMART analysis (Simple Modular Architecture Research Tool, http://smart.emblheidelberg.de/) (28), SwissProt database search, and search of the Conserved Domain Database using RPS-BLAST (http://www.ncbi.nlm.nih.gov/Structure/cdd/wrpsb.cgi), both mouse and human Hepp proteins lack any known domains or motifs, and do not have any obvious homology or structural similarities to known proteins. SignalP V1.1 Server (http://www.cbs.dtu.dk/services/SignalP/) did not predict the presence of N-terminal signal peptide or signal peptide cleavage sites in mouse and human Hepp protein. NetOGlyc 2.0 Server (http://www.cbs.dtu.dk/services/NetOGlyc/) has predicted one putative mucin type O-glycosylation site in mouse Hepp protein (Thr 213) and three putative O-glycosylation sites in human HEPP protein (Thr 81, 122, 217). NetPhos 2.0 protein phosphorylation prediction server (http://www.cbs.dtu.dk/services/NetPhos/), which predicts for serine, threonine, and tyrosine phosphorylation sites in eukaryotic proteins, has found 14 putative phosphorylation sites both in the mouse Hepp (Ser: 11; Thr: 2; Tyr: 1) and the human HEPP protein (Ser: 11; Thr: 2; Tyr: 1) (data not shown).

Identification and Analysis of Invertebrate and Vertebrate Orthologs of Hepp

Using the Proteome WormPD database (http://www.proteome.com/databases), DRES (Drosophila related expressed sequences) Search Engine (27) (http://hercules.tigem.it/DRES/dres.html) and Drosophila Genome Project Blast Search (http://www.fruitfly.org/cgi-bin/blast/public_blaster.pl) we were not able to identify a *C. elegans* or Drosophila ortholog of Hepp gene. By screening the Gen-Bank nonredundant database with mouse cDNA we have identified several rat (UniGene cluster Rn. 16249) and one zebrafish EST (Accession No. AW422282), similar to Hepp gene. All rat ESTs in cluster Rn. 16249 represent the 3' untranslated region (3' UTR) of rat Hepp cDNA and thus could not be conceptually translated and compared with mouse and human HEPP proteins. However, at the nucleotide sequence level 3' UTR of rat Hepp cDNA shares 88 and 86% identity with mouse and human HEPP cDNAs, respectively (data not shown). The zebrafish EST, representing partial cDNA, was conceptually translated, analyzed with SMART, and compared with protein sequence of mouse and human HEPP. ClustalW amino acid sequence alignment has shown that partial zebrafish Hepp protein shares 64% identity and 74% similarity with mouse Hepp protein, and 66% identity and 76% similarity with human HEPP protein (FIG. 3). The alignment of the N-terminal part of the zebrafish, mouse and human HEPP proteins demonstrates a high degree of evolutionary conservation of the amino terminal part of the protein and again shows several highly conserved contiguous blocks of amino acids (FIG. 3).

Expression Analysis of Hepp

Figure 4B:
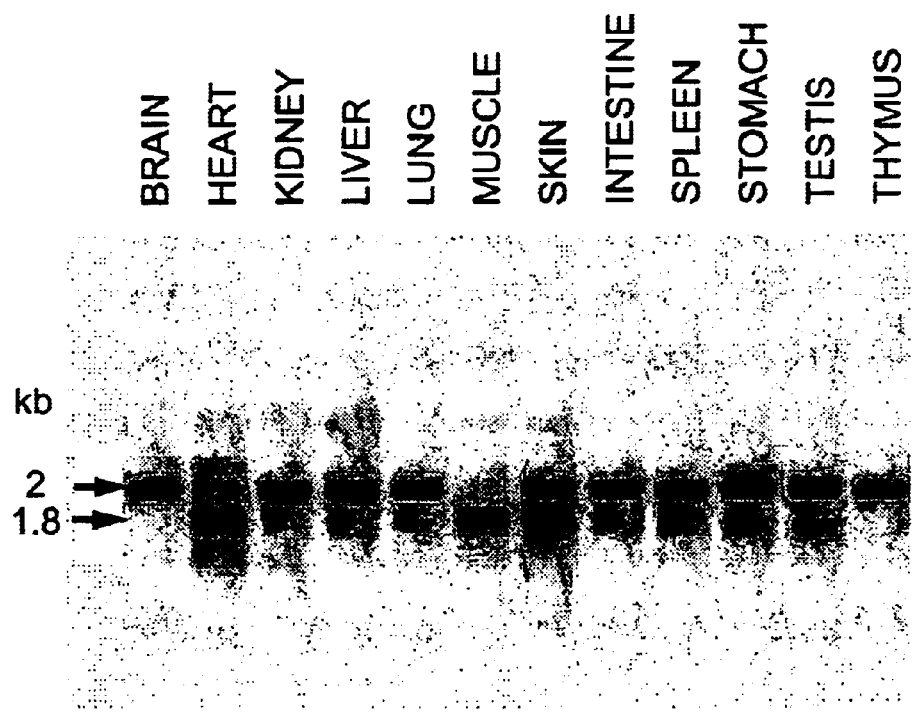

Hybridization of mouse multiple tissue Northern blot has revealed that Hepp is expressed at a very low level in the heart, lung, spleen and thymus, and at a higher level in the muscle. The heart and muscle express a larger ~4.8-kb transcript, whereas lung, spleen, and thymus express a smaller ~4-kb isoform, which probably arises through alternative splicing. Hepp transcripts are not detectable in the brain, kidney, liver, skin, intestine, stomach, and testis (FIG. 4). Since Hepp was found to be expressed preferentially in a progenitor cell population after the differential screening of subtracted Lin⁻Sca-1⁺ and Lin⁻Sca-1⁻ cell-specific libraries, it was important to reanalyze its expression in populations of mouse fetal and adult HSC and progenitors. Repetitive semi-quantitative duplex PCR analysis (using various dilutions of cDNA libraries as the template and 25–40 PCR cycles) has shown that Hepp is not expressed in mouse fetal liver HSC (Sca-1⁺c-kit⁺AA4.1⁺Lin⁻ cells), but is highly expressed in progenitor cell population (AA4.1⁻ cells) (FIG. 5). Similarly, using semi-quantitative duplex PCR with various dilutions of CDNA library and 25–40 PCR cycles, Hepp transcript was not detectable in highly purified population of Rh-123$^{low}$Sca-1⁺c-kit⁺Lin⁻ bone marrow cells. This population represents ~0.001% of normal bone marrow cells and is highly enriched for HSC activity (17, 29). Interestingly, expression of Hepp was found to be upregulated as more heterogeneous population of HSC and progenitors (Lin⁻Sea-1⁺ cells, representing 0.1–0.2% of normal bone marrow cells) differentiates into progenitors (Lin⁻Sca-1⁻ cells), as analyzed by semiquantitative duplex RT-PCR (FIG. 5). These findings confirm the results of differential screening of Lin⁻Sca-1⁺ and Lin⁻Sca-1⁻ cell-specific subtracted libraries. RT-PCR analysis of various hematopoietic cell lines has shown that Hepp is ubiquitously expressed in lymphoid progenitor, pro-B, pre-B and B cell lines including lymphomas, in T cell lymphoma cell lines and thymus, and in myeloid progenitor and monocyte-macrophage cell lines (FIG. 6).

Figure 7:
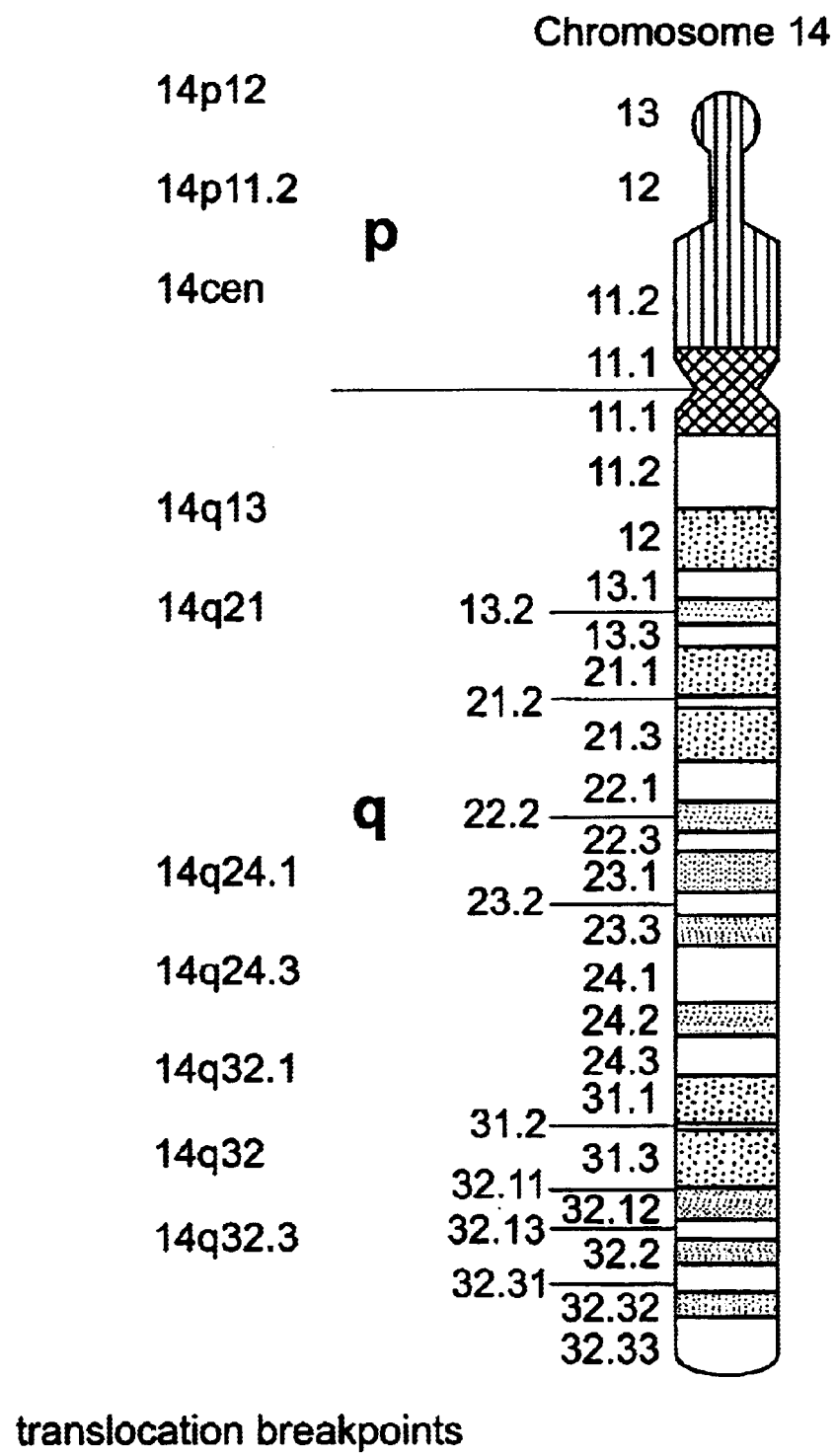
FIG. 7. Chromosomal localization of Hepp and hematological malignancies associated with rearrangements of the band q32 on chromosome 14.

Human HEPP Maps to Chromosomal Region with Frequent Chromosome Aberrations Associated with Multiple Cases of Various Hematological Malignancies Using the CELERA Gene Discovery System and BAC mapping it was determined that mouse Hepp gene maps to telomeric part of the chromosome 12, whereas human HEPP gene maps to q32 region on human chromosome 14, depicted in FIG. 7. According to Breakpoint Map of Recurrent Chromosome Aberrations database (http://www.ncbi.nlm.nih.gov/CCAP/mitelsum.cgi), band 14q32 represents a region with frequent balanced (translocations) and unbalanced chromosome aberrations (deletions, duplications) associated with multiple cases of various hematological malignancies (Table 1), for some of which the genes involved are unknown.

TABLE 1

| Neoplasm | Cases |
|---|---|
| Acute myelomonocytic leukemia | 5 |
| Lymphoblastic lymphoma | 13 |
| Chronic lymphocytic leukemia | 185 |
| Acute lymphoblastic leukemia | 316 |
| Multiple myeloma | 190 |
| B-prolymphocytic leukemia | 24 |
| Plasma cell leukemia | 35 |
| Adult T-cell lymphoma/leukemia | 31 |
| Diffuse large B-cell lymphoma | 324 |
| Nodal marginal zone B-cell lymphoma | 2 |
| Burkitt's lymphoma | 127 |
| Follicular lymphoma | 515 |
| Hairy cell leukemia | 8 |
| Mantle cell lymphoma | 158 |
| Splenic marginal zone B-cell lymphoma | 21 |
| T-prolymphocytic leukemia | 51 |

Mapping of the human HEPP to a chromosomal region with frequent chromosome aberrations associated with multiple cases of various hematological malignancies, suggests that HEPP is involved in etiology of some of the hematological malignancies.

Figure 8:
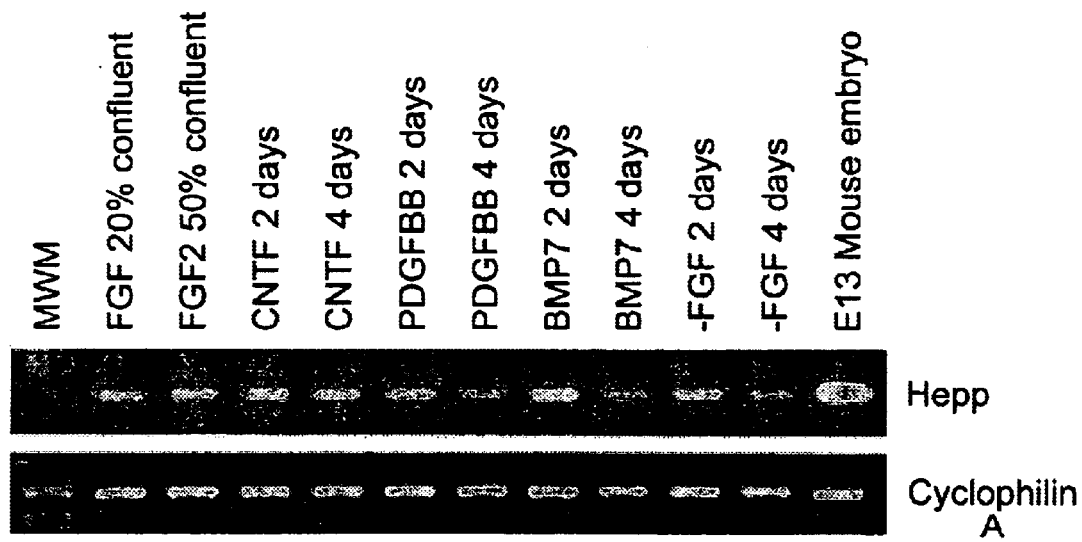
FIG. 8. Hepp is ubiquitously expressed in neural stem cells and progenitors and differentiated neural cell types.

Mouse Hepp is Expressed in Almost All Parts of Central and Peripheral Nervous System Throughout Embryonic Development and in Adult Mice, and is Expressed in Neural Stem Cells and Progenitors Expression of Hepp was analyzed in mouse fetal neural stem cells (NSC) and progenitors. Cultures of NSC and progenitors from E14 embryonic brain subventricular zone (SV) were established in the presence of bFGF (basic Fibroblast Growth Factor or FGF-2, necessary for NSC maintenance) and were induced to differentiate into neurons and glial cells by withdrawal of bFGF or by addition of ciliary neurotrophic factor (CNTF), platelet derived growth factor (PDGF-β) or bone morphogentic protein 7 (BMP7), cytokines used to drive differentiation of NSC in to neurons and glia cells in culture. Cyclophilin A was used as an internal positive control in RT-PCR. These experiments have established that Hepp is ubiquitously expressed in fetal NSC, progenitors and differentiated neural cell types (FIG. 8).

Figure 9:
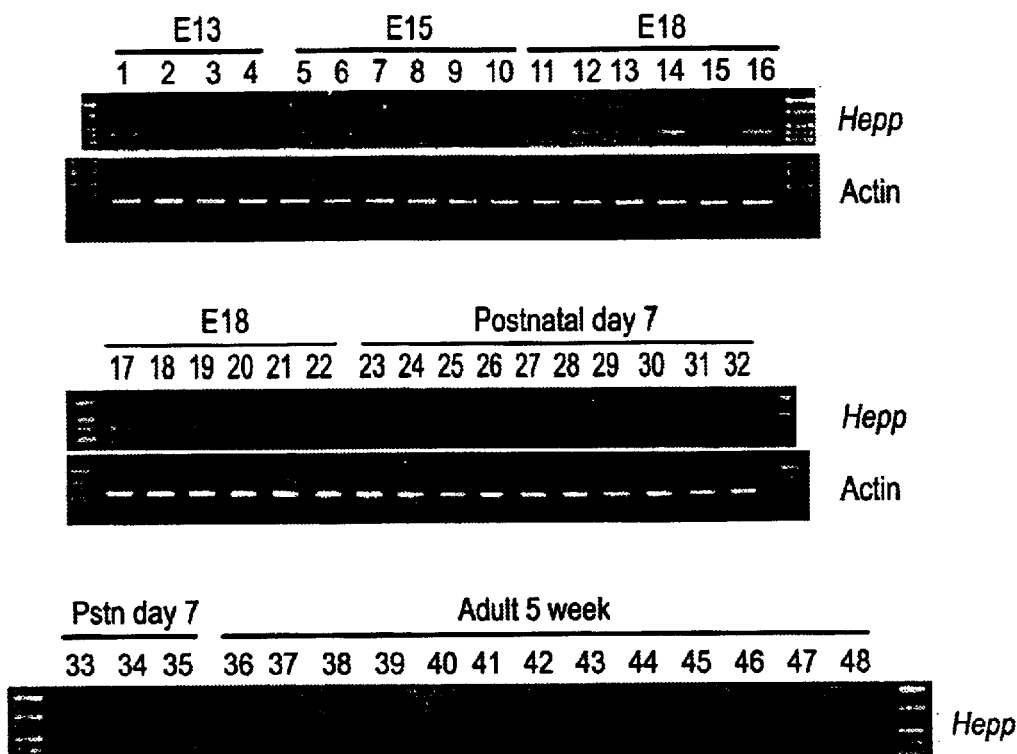
FIG. 9. Expression pattern of mouse Hepp in central and peripheral nervous system.

Using Mouse Brain Rapid-Scan Panel (OriGene Technologies), the expression pattern of Hepp in embryonic and adult central and peripheral nervous system was analyzed. The results demonstrated that Hepp is expressed in almost all parts of central and peripheral nervous system throughout embryonic development and in adult mice (including forebrain, midbrain, hindbrain, spinal cord) (FIG. 9).

Generation of Hepp Knockout Mice

Searching the database of trapped genes (Dr. William Skarnes, UC Berkeley) (http://socratesberkeley.edu/~starnes/resourse.html, we identified ES clone KST303 in which allele for HEPP was trapped by ATG-less secretory gene trap vector pGT1.8TM βgeo. The gene trap vector pGT1.8TM βgeo contains a splice acceptor sequence and transmembrane protein domain TM of CD4 gene upstream of a reporter and is activated following insertion into an intron. The analysis of trapping event in ES cell clone KST303 showed proper splicing of the integrated vector and fusion of the βgeo reporter to the 5' UTR of HEPP transcript, which should result in severely truncated transcript and absence of functional HEPP protein. Using ES cell clone KST303 we generated HEPP knockout mice. ES clones with targeted Hepp alleles can be generated by routine means by a practitioner skilled in gene targeting techniques. (See, for example, Gene Knockout Protocols. In: Methods in Molecular Biology, vol. 158, 2001. Edited by: M. J. Tymms and I. Kola. Humana Press, Totowa, N.J.)

Figure 10A:
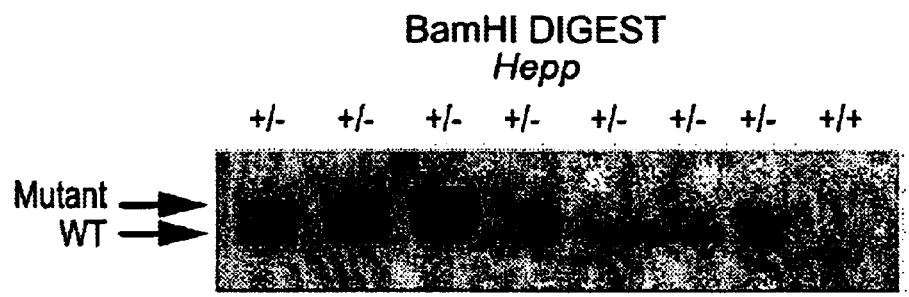
FIG. 10. Genotyping of the progeny from the breeding of heterozygous Hepp+/− mice.
Figure 10B:
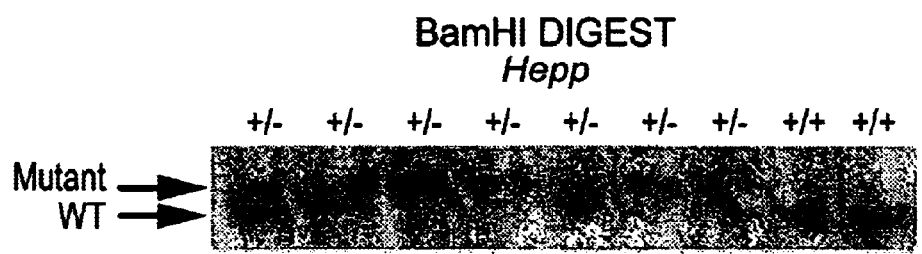

Viable heterozygous Hepp mice were bred to generate Hepp −/− mice (FIG. 10). Genotyping of progeny from breeding of Hepp$^{+/-}$ mice has revealed that the vast majority (80%) of Hepp$^{-/-}$ mice die in utero (FIG. 10; Table 2).

TABLE 2

Genotyping and ratio of adult Hepp$^{+/+}$, Hepp$^{+/-}$ and Hepp$^{-/-}$ mice.

| Genotype → | Hepp$^{+/+}$ | Hepp$^{+/-}$ | Hepp$^{-/-}$ | Total |
|---|---|---|---|---|
| Number of mice | 15 | 34 | 3 | 52 |
| Experimental Mendelian ratio | 23.5% | 53% | 4.7% | |
| Theoretical Mendelian ratio | 16 (25%) 1 | 32 (50%) 2 | 16 (25%) 1 | 64 |

Analysis of Hematopoietic System in Hepp KO Mice

Figure 11:
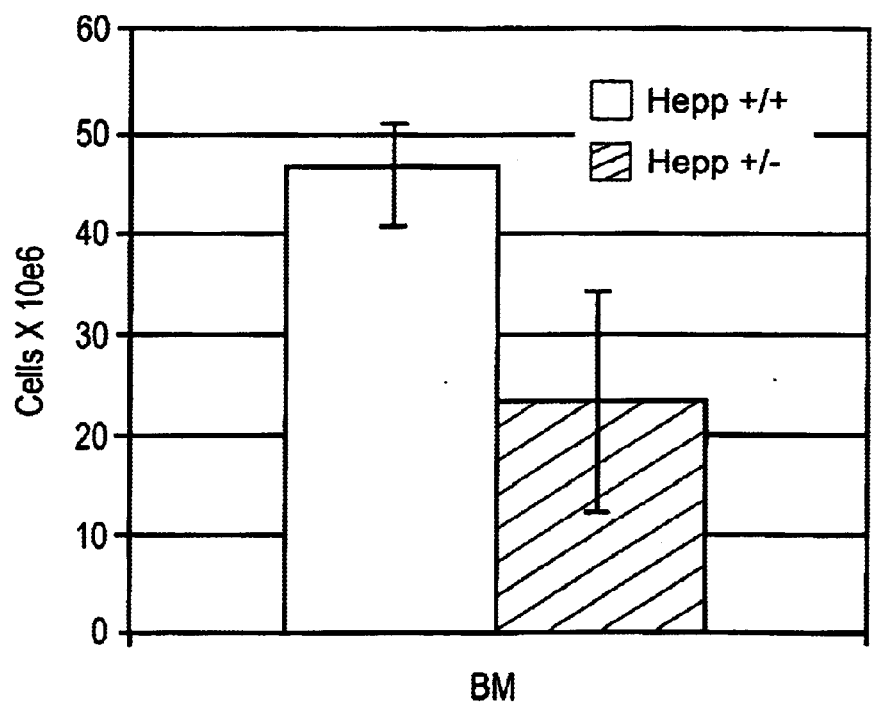
FIG. 11. Significantly reduced number of BM cells in femurs and tibias of Hepp+/− mice.

The analysis of 23 Hepp$^{+/-}$ mice revealed perturbed hematopoiesis consisting of bone marrow cytopenia, overproduction and/or accumulation of hematopoietic progenitors, and splenomegaly with follicular hyperplasia. In addition, Hepp$^{+/-}$ mice have significantly reduced number of bone marrow (BM) cells in femurs and tibias (FIG. 11).

Figure 12:
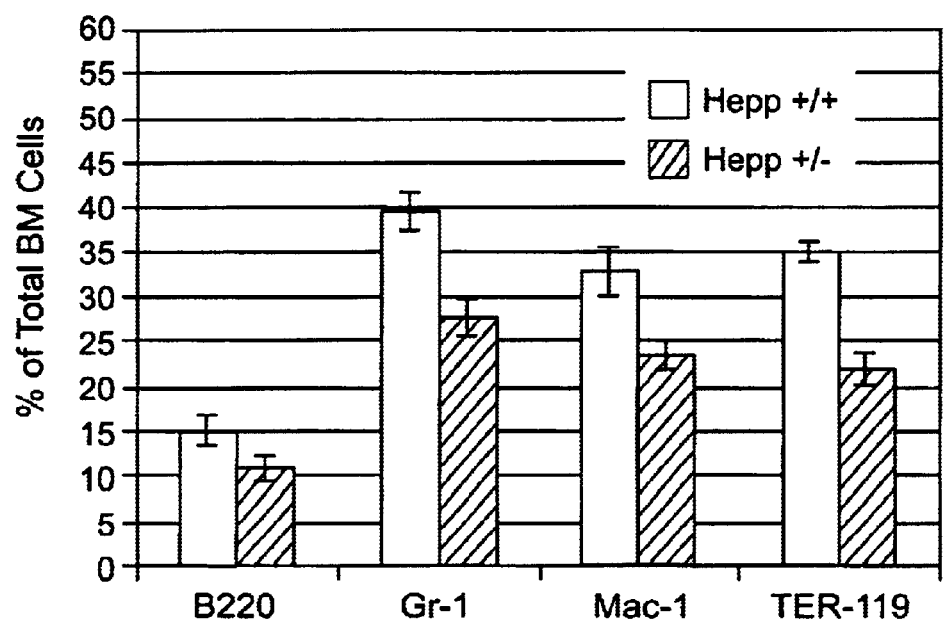
FIG. 12. Decreased content of B cells, granulocytes, macrophages and erythroblasts in the BM of Hepp+/− mice (flow cytometry analysis).
Figure 13:
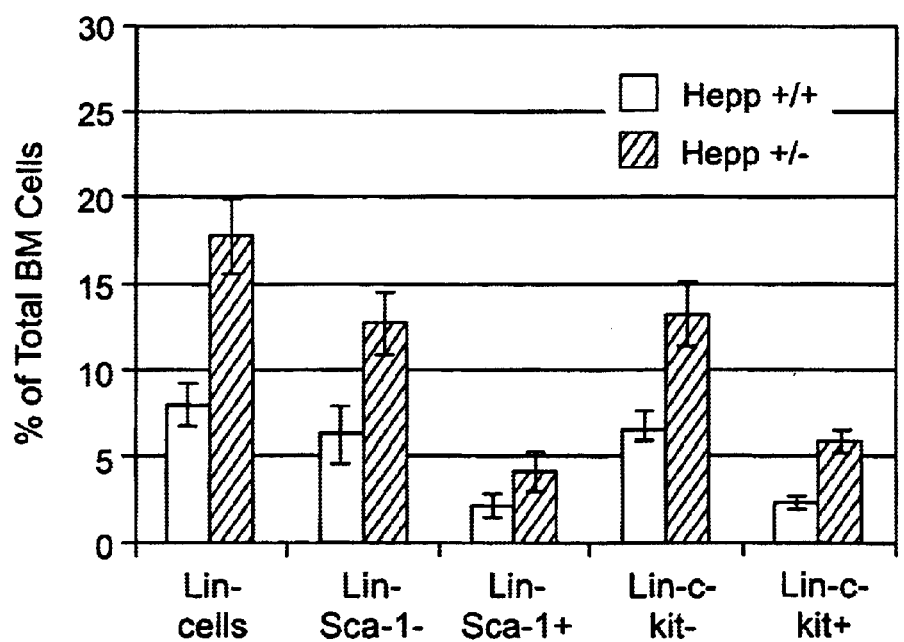
FIG. 13. Increased content of BM cell populations containing progenitors and HSC in Hepp+/− mice as analyzed by flow cytometry.
Figure 14:
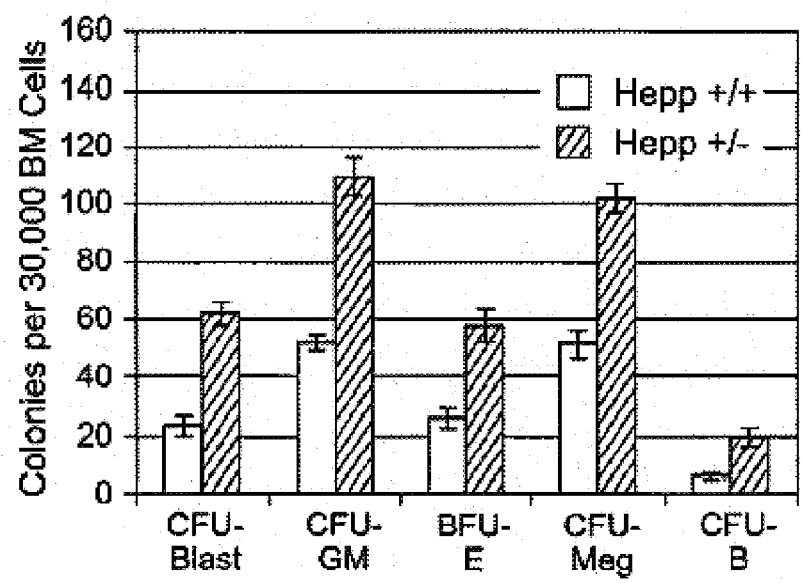
FIG. 14. Increased content of myelo-erythroid and lymphoid progenitors in the BM of Hepp+/− mice (colony-forming assays)

Flow cytometry analysis revealed decreased content of B cells, granulocytes, macrophages and erythroblasts in the BM of HeppU+/− mice (FIG. 12). In contrast, the content of BM cell populations containing (a) immature hematopoietic cells (lineage negative Lin$^-$ cells), (b) early and late progenitors (Lin$^-$Sca-1$^-$ and Lin$^-$c-kit$^-$ cells), and (c) early progenitors and HSC (Lin$^-$Sca-1$^+$ and Lin$^-$c-kit$^+$ cells) was increased in Hepp$^{+/-}$ mice (FIG. 13). Furthermore, colony-forming assays demonstrated increased content of blast colony-forming (CFU-Blast), myelo-erythroid (CFU-GM, BFU-E and CFU-Meg) and lymphoid (CFU-B) progenitors in the BM from Hepp$^{+/-}$ mice (FIG. 14).

Figure 15A:
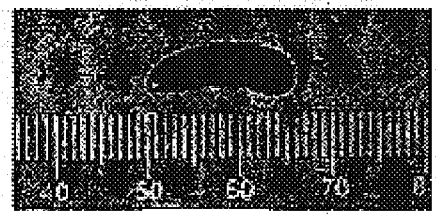
FIGS. 15A–B. Splenomegaly in Hepp+/− mice. Spleens of Hepp+/+ (15A) and Hepp+/− (15B) mice FIG. 15C. Significantly increased number of splenocytes in Hepp+/− mice.
Figure 15B:
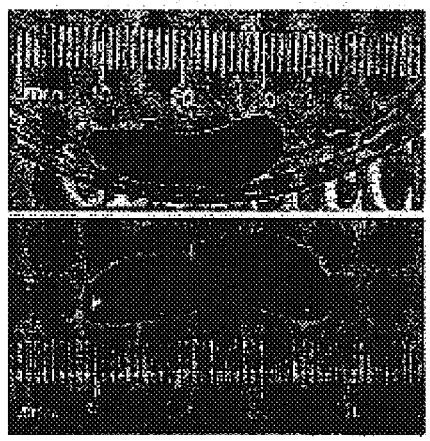
Figure 15C:
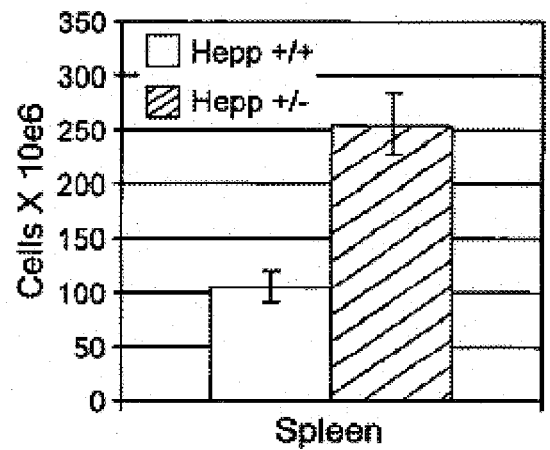
Figure 16A:
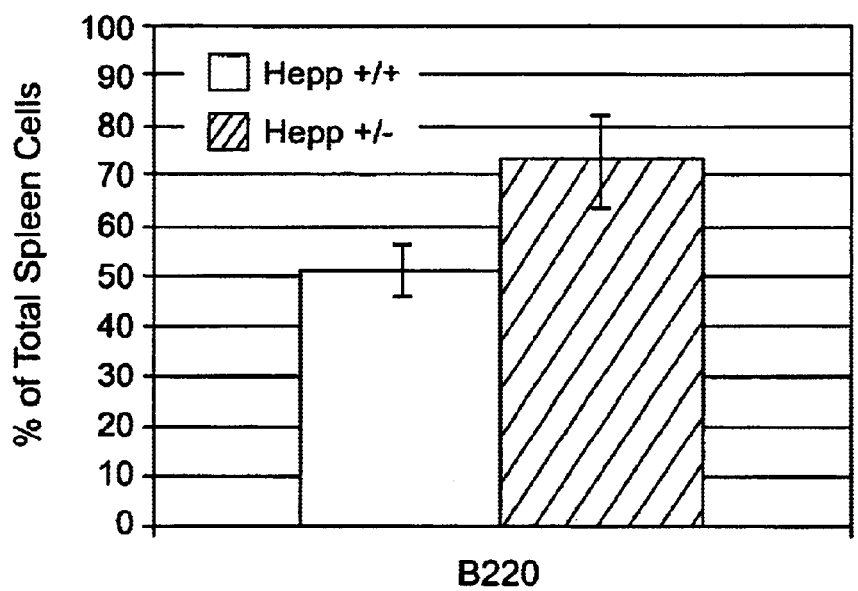
FIG. 16. Increased content of B220+ cells in the spleen of Hepp+/− mice (flow cytometry analysis).
Figure 16B:
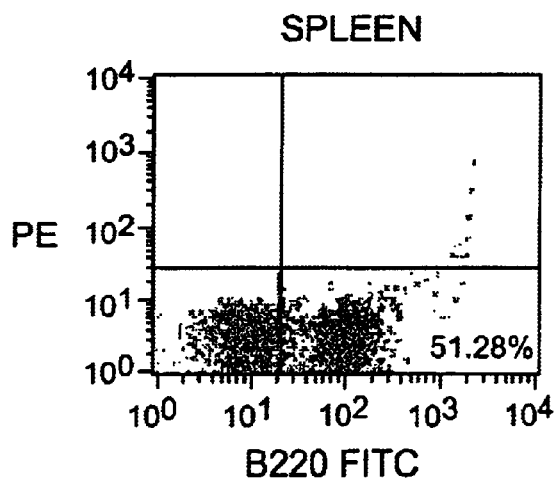
Figure 16C:
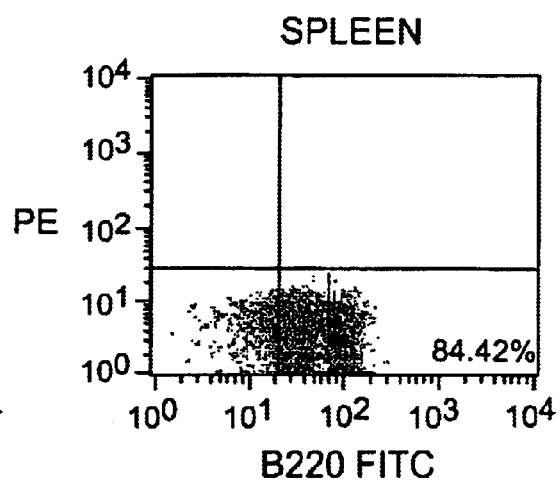
Figure 17A:
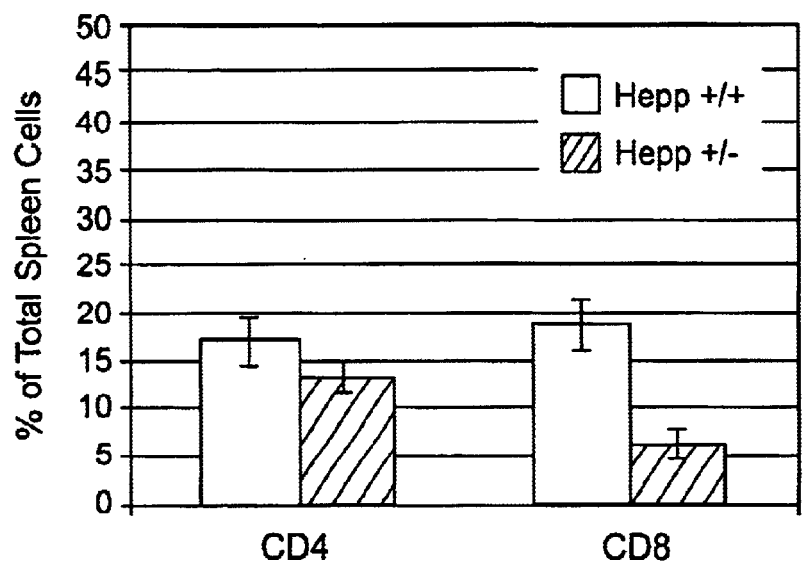
FIG. 17. Decreased content of CD8+ T cells in the spleen of Hepp+/− mice (flow cytometry analysis).
Figure 17B:
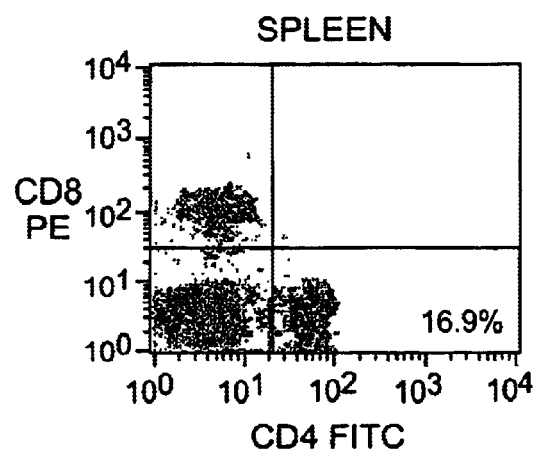
Figure 17C:
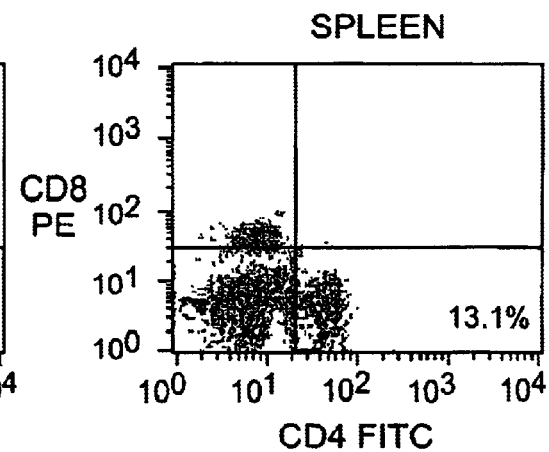

Another readily observable feature was very frequent splenomegaly in Hepp$^{+/-}$ mice, with significantly increased number of splenocytes and follicular hyperplasia (FIG. 15). This follicular hyperplasia was accompanied by increased content of B220$^+$ cells in the spleen of Hepp$^{+/-}$ mice as analyzed by flow cytometry (FIG. 16). Flow cytometry analysis of myeloid cells (granulocytes, macrophages and erythroblasts) in the spleen did not show any difference between wild type and Hepp$^{+/-}$ mice (data not shown). We have also observed slight decrease in the content of CD4$^+$ T cells and significantly decreased content of CD8$^+$ T cells in the spleen of Hepp$^{+/-}$ mice as analyzed by flow cytometry (FIG. 17).

Analysis of Central and Peripheral Nervous System in Hepp KO Mice

The last facet of the phenotype is progressive neuromuscular degeneration in Hepp +/−mice. About 40% of Hepp$^{+/-}$ mice show slight tremor, impaired balance during walking, and very mild paralysis of hind legs. Mice have difficulty turning over when placed on their backs in a supine position.

Figure 18A:
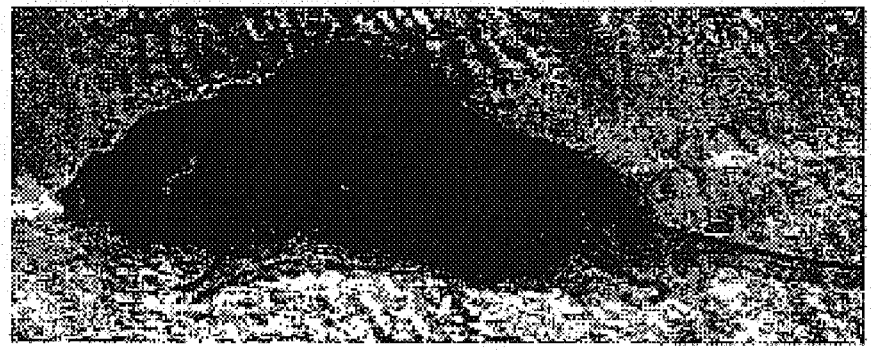
FIG. 18. Progressive neurodegenerative disease in affected Hepp+/− mice.
Figure 18B:
Figure 18C:
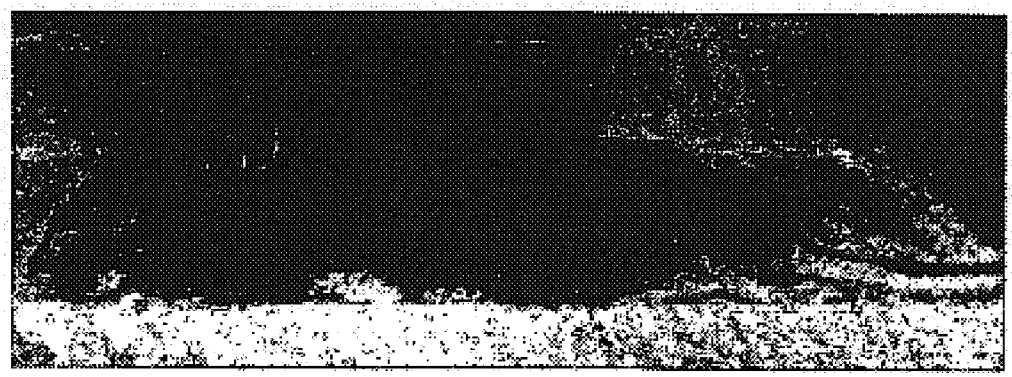

After 4 months of age about 10% of affected Hepp$^{+/-}$ mice exhibit full paralysis of hind legs, seizures, severe muscular atrophy and wasting (FIG. 18). Mice with full penetrance of the progressive neurodegenerative disease do not survive beyond 6 months of age. A review of current literature and mouse models (e.g. mice lacking hypoxia-response element of VEGF; Oosthuyse B, Moons L, Storkebaum E, et al. (2001). Deletion of the hypoxia-response element in the vascular endothelial growth factor promoter causes motor neuron degeneration. Nat. Genet. Jun. 28, 2001(2):131–138), supports the conclusion that adult-onset progressive neurodegenerative disease in Hepp$^{+/-}$ mice has features that closely resemble amyotrophic lateral sclerosis (ALS). Accordingly, these mice show promise of being a useful model for the study of this human disease.

Conclusions

In summary, the multifaceted phenotype of Hepp$^{+/-}$ mice consists of at least the following features:

1. Skeletal defects and growth retardation, indicating that Hepp plays a role in embryonic development,
2. Perturbed hematopoiesis that encompasses: bone marrow cytopenia, overproduction and accumulation of hematopoietic progenitors, and splenomegaly with follicular hyperplasia, and
3. Adult-onset progressive neurodegenerative disease reminiscent of amyotrophic lateral sclerosis (ALS), which suggests a role for Hepp in neuronal development and function.

The complex phenotype of Hepp KO mice suggests that Hepp is a part of common molecular mechanism utilized in the development and differentiation of hematopoietic and neuronal cells and perhaps other cell types as well.

Discussion

Differential screening of subtracted cDNA libraries from mouse fetal and adult cell populations enriched for HSC and progenitors and sequencing of differentially expressed clones have already yielded a number of both novel as well as evolutionarily conserved genes, present from Drosophila to humans (16, 17, 19, 31). Described herein is the cloning and characterization of a novel gene, Hepp, identified through differential screening of subtracted cDNA libraries from mouse adult bone marrow cell populations enriched for HSC (Lin$^-$Sca-1$^+$ cells) and progenitors (Lin$^{-Sca-}$1$^-$ cells) (19). Mouse Hepp and human HEPP transcripts encode novel conserved proteins without any known structural or functional domains or motifs, and lacking any obvious homology or structural similarities to known proteins. Furthermore, lack of invertebrate orthologs and a high degree of evolutionary conservation of the peptide sequence in zebrafish, mouse and humans suggest that in vertebrates Hepp gene has an important conserved although as yet not completely elucidated function. Differential screening of mouse bone marrow HSC (Lin$^-$Sca-1$^+$) and progenitor (Lin$^-$Sca-1$^-$) cell-specific subtracted cDNA libraries has demonstrated that Hepp is expressed preferentially in progenitor cell populations (Lin$^-$Sca-1$^-$ cells). During embryonic blood cell development Hepp is not expressed in the population of mouse fetal liver HSC (Sca-1$^+$c-kit$^+$AA4.1$^+$Lin$^-$ cells), but is abundantly transcribed in fetal liver progenitors and mature blood cells (AA4.1$^-$ cells). These results are in agreement with the fact that in the BLAST search of the Stem Cell Database (SCDB; http://stemcell.princeton.edu/; Dr. Ihor Lemischka, Princeton University) mouse Hepp cDNA did not match any ESTs derived from the Sca-1$^+$c-kit$^+$AA4.1$^+$Lin$^-$ cell-specific subtracted library, containing transcripts expressed preferentially in mouse fetal liver HSC population (17, 30).

Similarly, during adult mouse hematopoiesis, Hepp is not transcribed in the population of Rho-1231$^{low}$Sca-1$^+$c-kit$^+$Lin$^-$cells (representing ~0.001% of normal bone marrow cells and highly enriched for HSC) (17, 29), but is expressed at low level in more heterogeneous population of Lin$^{-Sca-}$1$^+$ cells (representing 0.1–0.2% of normal bone marrow cells and enriched for HSC and progenitors). Hepp transcription is upregulated in progenitor cell population (Lin$^-$Sca-1$^-$ cells) and in various lymphoid and myeloid cell lines. Therefore, mouse Hepp exhibits developmentally regulated pattern and conservation of preferential expression in both fetal and adult hematopoietic progenitors and mature blood cells during embryonic and adult hematopoiesis. Restricted expression pattern in tissues and preferential expression in mouse fetal and adult hematopoietic progenitors and mature blood cells suggest that mouse Hepp is involved in the regulation of HSC and progenitor cell lineage commitment and differentiation.

In describing preferred embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. Each reference cited herein is incorporated by reference as if each were individually incorporated by reference.

The embodiments illustrated and discussed in the present specification are intended only to teach those skilled in the art the best way known to the inventors to make and use the invention, and should not be considered as limiting the scope of the present invention. The exemplified embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

REFERENCES

References cited herein are listed below for convenience and are hereby incorporated by reference.

1. Orkin, S. H. (1996) Development of the hematopoietic system. Curr. Opin. Genet. Dev. 6, 597–602.
2. Morrison, S. J., Wright, D. E., Cheshier, S. H., and Weissman, I. L. (1997) Hematopoietic stem cells: Challenges to expectations. Curr. Opin. Immunol. 9, 216–221.
3. Morrison, S. J., Shah, N. M., and Anderson, D. J. (1997) Regulatory mechanisms in stem cell biology. Cell 88, 287–298.
4. Kondo, M., Weissman, I. L., and Akashi, K. (1997) Identification of clonogenic common lymphoid progenitors in mouse bone marrow. Cell 91, 661–672.
5. Akashi, K., Traver, D., Miyamoto, T., and Weissman, I. L. (2000) A clonogenic common myeloid progenitor that gives rise to all myeloid lineages. Nature 404, 193–197.
6. Weiss, M. J., and Orkin, S. H. (1995) GATA transcription factors: Key regulators of hematopoiesis. Exp. Hematol. 23, 99–107.
7. Watowich, S. S., Wu, H., Socolovsky, M., Klingmuller, U., Constantinescu, S. N., and Lodish, H. F. (1996) Cytokine receptor signal transduction and the control of hematopoietic cell development. Annu. Rev. Cell Dev. Biol. 12, 91–128.
8. Tenen, D. G., Hromas, R., Licht, J. D., and Zhang, D. E. (1997) Transcription factors, normal myeloid development, and leukemia. Blood 90, 489–519.
9. Glimcher, L. H., and Singh, H. (1999) Transcription factors in lymphocyte development—T and B cells get together. Cell 96, 13–23.
10. Rothenberg, E. V. (1999) Stepwise specification of lymphocyte developmental lineages. Curr. Opin. Genet. Dev. 10, 370–379.
11. Kuo, C. T., and Leiden, J. M. (1999) Transcriptional regulation of T lymphocyte development and function. Annu. Rev. Immunol. 17, 149–187.
12. Cortes, M., Wong, E., Koipally, J., and Georgopoulos, K. (1999) Control of lymphocyte development by the Ikaros gene family. Curr. Opin. Immunol. 11, 167–171.
13. Busslinger, M., Nutt, S. L., and Rolink, A. G. (2000) Lineage commitment in lymphopoiesis. Curr. Opin. Immunol. 12, 151–158.
14. O'Riordan, M., and Grosschedl, R. (2000) Transcriptional regulation of early B-lymphocyte differentiation. Immunol. Rev. 175, 94–103.
15. Kondo, M., Scherer, D. C., Miyamoto, T., King, A. G., Akashi, K., Sugamura, K., and Weissman, I. L. (2000) Cell-fate conversion of lymphoid-committed progenitors by instructive actions of cytokines. Nature 407, 383–386.
16. Lemischka, I. (1999) Searching for stem cell regulatory molecules. Ann. N.Y. Acad. Sci. 872, 274–287.
17. Phillips, R. L., Ernst, R. E., Brunk, B., Ivanova, N., Mahan, M. A., Deanehan, J. K., Moore, K. A., Overton, G. C., and Lemischka, I. R. (2000) The genetic program of hematopoietic stem cells. Science 288, 1635–1640.
18. Weissman, I. L. (2000) Translating stem and progenitor cell biology to the clinic: Barriers and opportunities. Science 287, 1442–1446.
19. Abdullah, J. M., Li, X., Nachtman, R. G., and Jurecic, R. (2001) FLRF, a novel evolutionarily conserved ring finger gene, is differentially expressed in mouse fetal and adult hematopoietic stem cells and progenitors. Blood Cells Mol. Dis. 27, 320–333.
20. Spangrude, G. J., and Scollay, R. (1990) A simplified method for enrichment of mouse hematopoietic stem cells. Exp. Hematol. 18, 920–926.

21. Jurecic, R., Van, N. T., and Belmont, J. W. (1993) Enrichment and functional characterization of Sca-1+ WGA+, Lin−WGA+, Lin−Sca-1+, and Lin−Sca-1+WGA+ bone marrow cells from mice with an Ly-6a haplotype. *Blood* 82, 2673–2683.

22. Rebel, V. I., Dragowska, W., Eaves, C. J., Humphries, R. K., and Lansdorp, P. M. (1994) Amplification of Sca-1+ Lin−WGA+ cells in serum-free cultures containing steel factor, interleukin-6, and erythropoietin with maintenance of cells with long-term in vivo reconstituting potential. *Blood* 83, 128–136.

23. Li, C. L., and Johnson, G. R. (1995) Murine hematopoietic stem and progenitor cells: I. Enrichment and biologic characterization. *Blood* 85, 1472–1479.

24. Munroe, D. J., Loebbert, R., Bric, E., Whitton, T., Prawitt, D., Vu, D., Buckler, A., Winterpacht, A., Zabel, B., and Housman, D. E. (1995) Systematic screening of an arrayed cDNA library by PCR. *Proc. Natl. Acad. Sci. USA* 92, 2209–2213.

25. Diatchenko, L., Lau, Y. F., Campbell, A. P., Chenchik, A., Moqadam, F., Huang, B., Lukyanov, S., Lukyanov, K., Gurskaya, N., Sverdlov, E. D., and Siebert, P. D. (1996) Suppression subtractive hybridization: A method for generating differentially regulated or tissue-specific cDNA probes and libraries. *Proc. Natl. Acad. Sci. USA* 93, 6025–6030.

26. Diatchenko, L., Lukyanov, S., Lau, Y. F., and Siebert, P. D. (1999) Suppression subtractive hybridization: A versatile method for identifying differentially expressed genes. *Methods Enzymol.* 303, 349–380.

27. Banfi, S., Borsani, G., Rossi, E., Bernard, L., Guffanti, A., Rubboli, F., Marchitiello, A., Giglio, S., Coluccia, E., Zollo, M., Zuffardi, O., and Ballabio, A. (1996) Identification and mapping of human cDNAs homologous to Drosophila mutant genes through EST database searching. *Nat. Genet.* 13, 167–174.

28. Schultz, J., Copley, R. R., Doerks, T., Ponting, C. P., and Bork, P. (2000) SMART: A Web-based tool for the study of genetically mobile domains. *Nucleic Acids Res.* 28, 231–234.

29. Kim, M., Cooper, D. D., Hayes, S. F., and Spangrude, G. J. (1998) Rhodamine-123 staining in hematopoietic stem cells of young mice indicates mitochondrial activation rather than dye efflux. *Blood* 91, 4106–4117.

30. Jordan, C. T., Astle, C. M., Zawadzki, J., Mackarehtschian, K., Lemischka, I. R., and Harrison, D. E. (1995) Long-term repopulating abilities of enriched fetal liver stem cells measured by competitive repopulation. *Exp. Hematol.* 23, 1011–1015.

31. Wiesmann, A., Phillips, R. L., Mojica, M., Pierce, L. J., Searles, A. E., Spangrude, G. J., and Lemischka, I. (2000) Expression of CD27 on murine hematopoietic stem and progenitor cells. *Immunity* 12, 193–199.

32. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. *Nucleic Acids Research* 22, 4673-4680).

What is claimed is:

1. An isolated nucleic acid comprising a sequence that is at least 98% identical to SEQ ID NO:1, or a sequence that is complementary over the entire length of SEQ ID NO:1, or a sequence that due to the degeneracy of the genetic code encodes an identical polypeptide product to that encoded by SEQ ID NO:1.

2. The nucleic acid of claim 1 comprising a sequence that is at least 99% identical to SEQ ID NO:1, or a sequence that is complementary over the entire length of SEQ ID NO:1, or a sequence that due to the degeneracy of the genetic code encodes an identical polypeptide product to that encoded by SEQ ID NO:1.

3. The nucleic acid of claim 2 comprising a sequence that is identical to SEQ ID NO:1, or a sequence that is complementary over the entire length of SEQ ID NO:1, or a sequence that due to the degeneracy of the genetic code encodes an identical polypeptide product to that encoded by SEQ ID NO:1.

4. The nucleic acid of claim 3 that is identical to SEQ ID NO:1.

5. The nucleic acid of claim 3 that is complementary to SEQ ID NO:1 over the entire length of SEQ ID NO:1.

6. The nucleic acid of claim 3 that due to the degeneracy of the genetic code encodes an identical polypeptide product to that encoded by SEQ ID NO:1.

* * * * *